(12) United States Patent
Agrawal

(10) Patent No.: US 11,753,613 B2
(45) Date of Patent: Sep. 12, 2023

(54) METHODS AND DEVICES FOR GENERATING CHEMICAL AND GASEOUS GRADIENTS IN MICROFLUIDIC PLATFORMS

(71) Applicant: Children's National Medical Center, Washington, DC (US)

(72) Inventor: Nitin Agrawal, Fairfax, VA (US)

(73) Assignee: Children's National Medical Center, Washington, DC (US)

( * ) Notice: Subject to any disclaimer, the term of this patent is extended or adjusted under 35 U.S.C. 154(b) by 1345 days.

(21) Appl. No.: 16/183,204

(22) Filed: Nov. 7, 2018

(65) Prior Publication Data

US 2019/0136177 A1 May 9, 2019

Related U.S. Application Data

(60) Provisional application No. 62/582,394, filed on Nov. 7, 2017.

(51) Int. Cl.
| | |
|---|---|
| *C12M 1/34* | (2006.01) |
| *C12M 3/06* | (2006.01) |
| *C12M 1/12* | (2006.01) |
| *C12M 1/04* | (2006.01) |
| *C12N 5/00* | (2006.01) |
| *C12M 1/107* | (2006.01) |
| *C12M 1/00* | (2006.01) |

(52) U.S. Cl.
CPC ............ *C12M 41/34* (2013.01); *C12M 23/16* (2013.01); *C12M 23/20* (2013.01); *C12M 23/24* (2013.01); *C12M 23/34* (2013.01); *C12M 23/36* (2013.01); *C12M 25/02* (2013.01); *C12M 41/32* (2013.01); *C12N 5/0075* (2013.01)

(58) Field of Classification Search
CPC ...... C12M 41/34; C12M 41/32; C12M 23/16; C12M 23/20; C12M 23/24; C12M 23/34; C12M 23/36; C12M 25/02; C12N 5/0075
USPC ........................................................ 435/374
See application file for complete search history.

(56) References Cited

U.S. PATENT DOCUMENTS 9,632,076 B2 * 4/2017 Achyuta ................ C12M 41/34
9,829,451 B2 * 11/2017 Gray ...................... G01N 21/01
(Continued)

OTHER PUBLICATIONS

Sinkala and Eddington, Oxygen sensitive microwells, 2010, Royal Society of Chemistry, Lab on a Chip (Year: 2010).*
Sinkala et al. (2010) (Year: 2010).*

*Primary Examiner* — Michael L Hobbs
*Assistant Examiner* — Lenora A Abel
(74) *Attorney, Agent, or Firm* — Oblon, McClelland, Maier & Neustadt, L.L.P.

(57) ABSTRACT

Disclosed herein are devices, methods and compositions for making and using microfluidic devices comprising making a microfluid device comprising one or more channels; and coating at least a portion of an interior surface of at least one channel, wherein one or more gradients are formed by simultaneously introducing into the device a first cellular culture media composition having a certain concentration of a gas, an active agent or both and a second composition having a concentration of a gas, an active agent or both that is/are different from that of the first composition. Such devices are used to investigate cellular responses to physiological states and active agents.

8 Claims, 18 Drawing Sheets

(56) References Cited

U.S. PATENT DOCUMENTS

2004/0106192 A1\* 6/2004 Jeon ................ B01L 3/502707
435/305.2
2006/0000709 A1\* 1/2006 Bohm ................ F16K 99/0001
422/68.1

\* cited by examiner

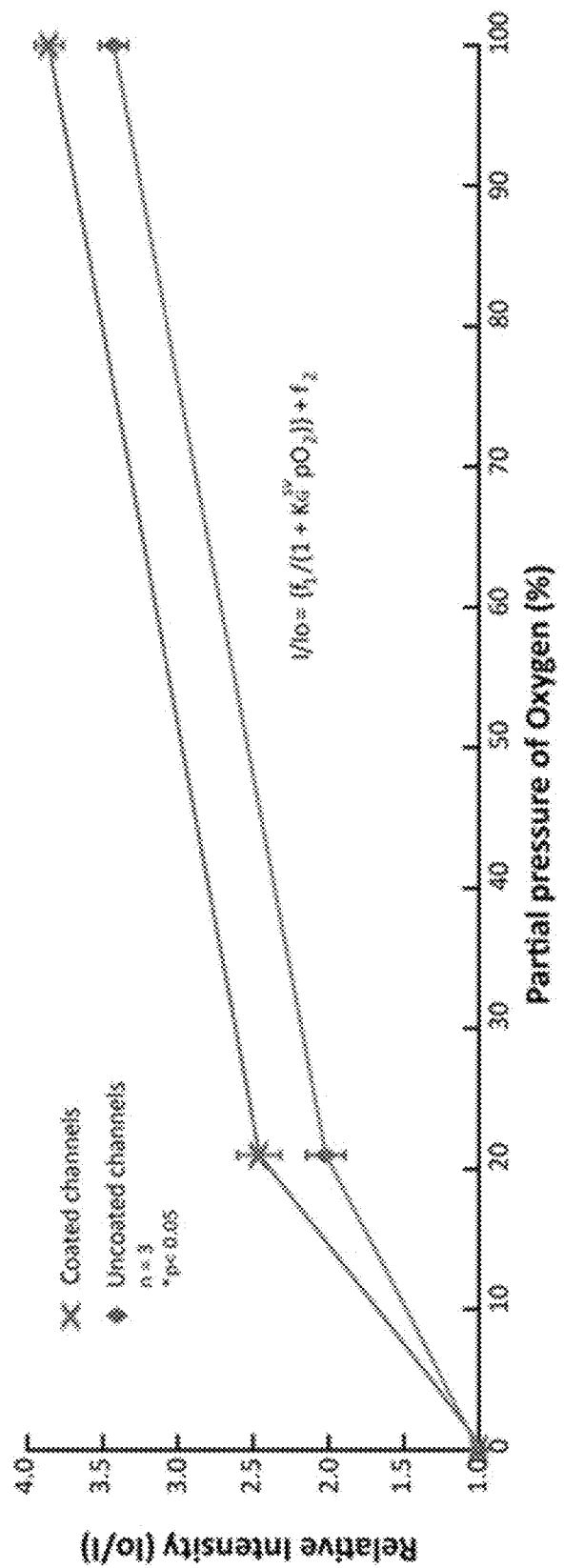
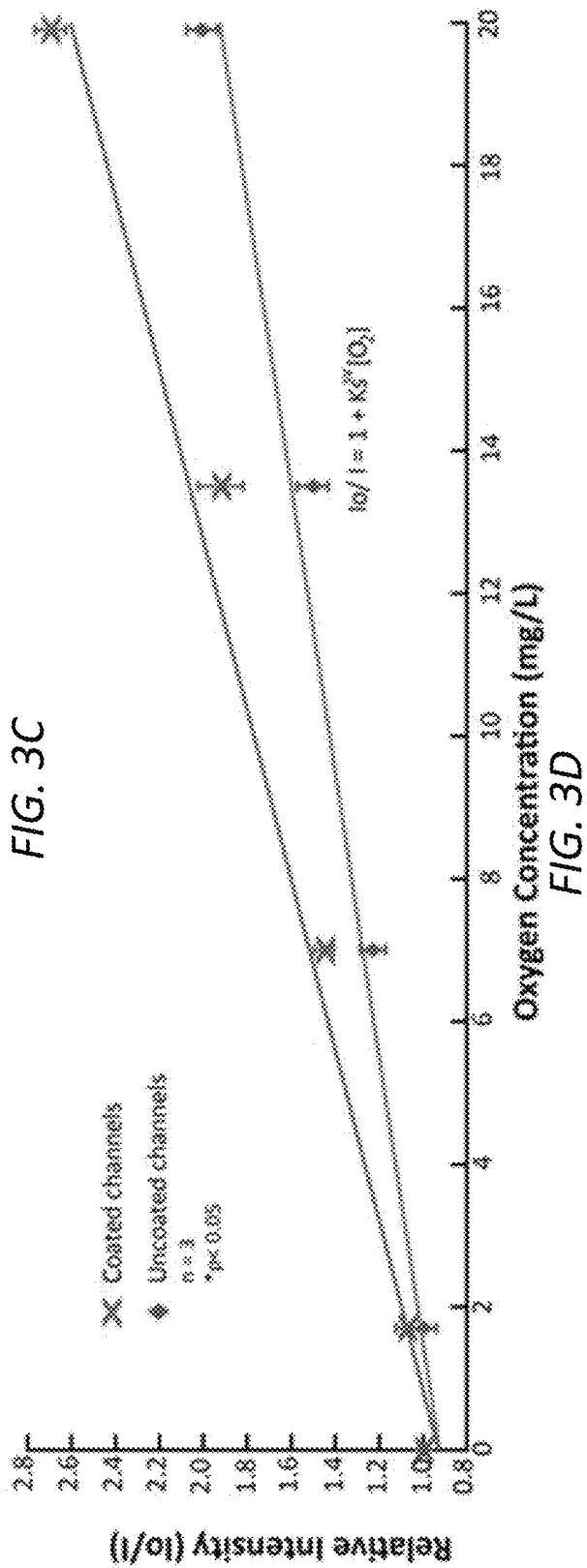
FIG. 3C
FIG. 3D

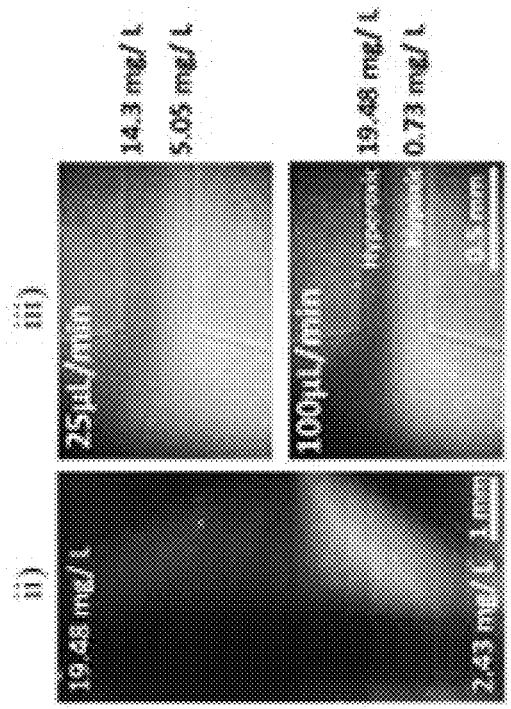
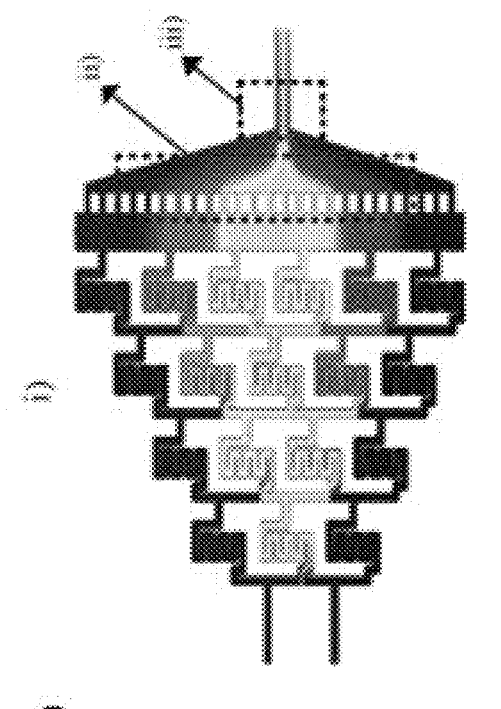
FIG. 4A
FIG. 4B

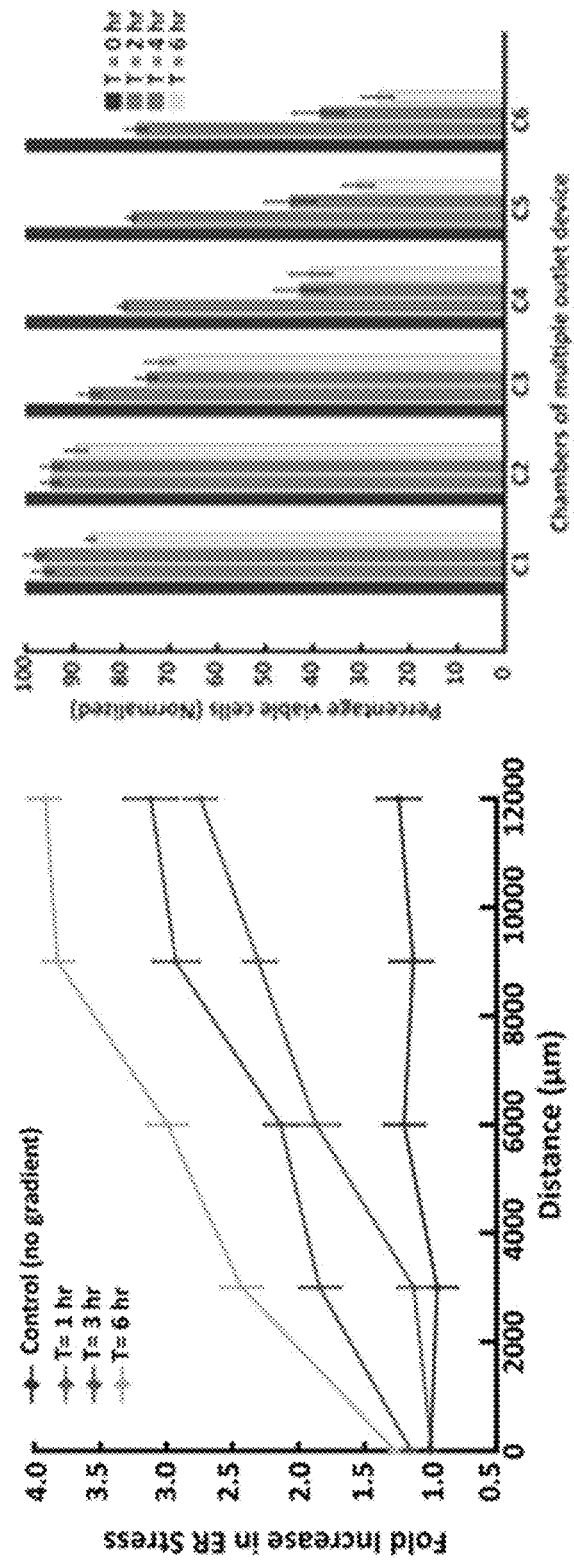
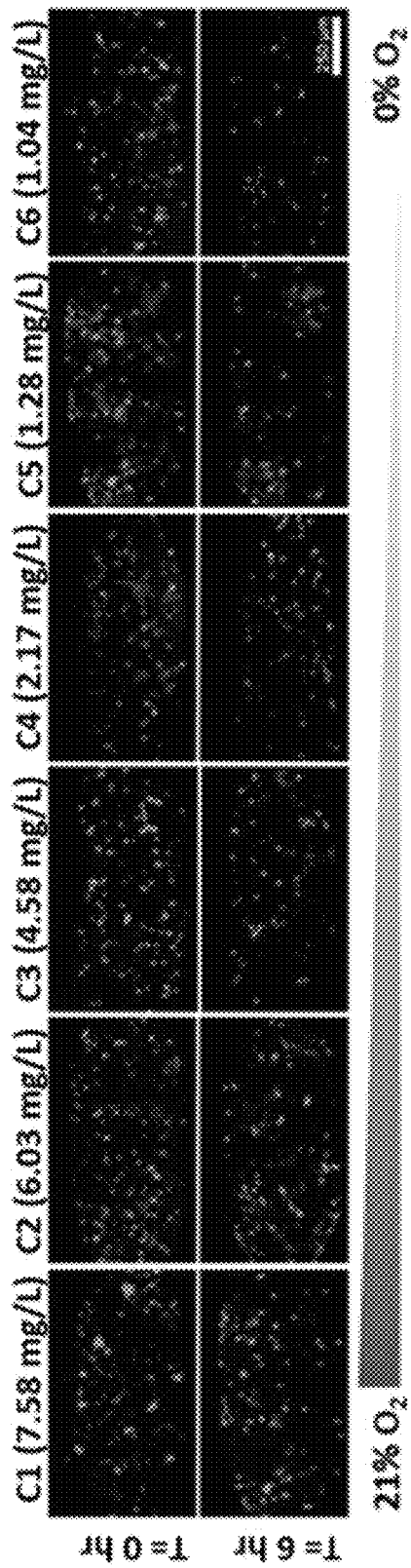
FIG. 5C
FIG. 5E
FIG. 5D

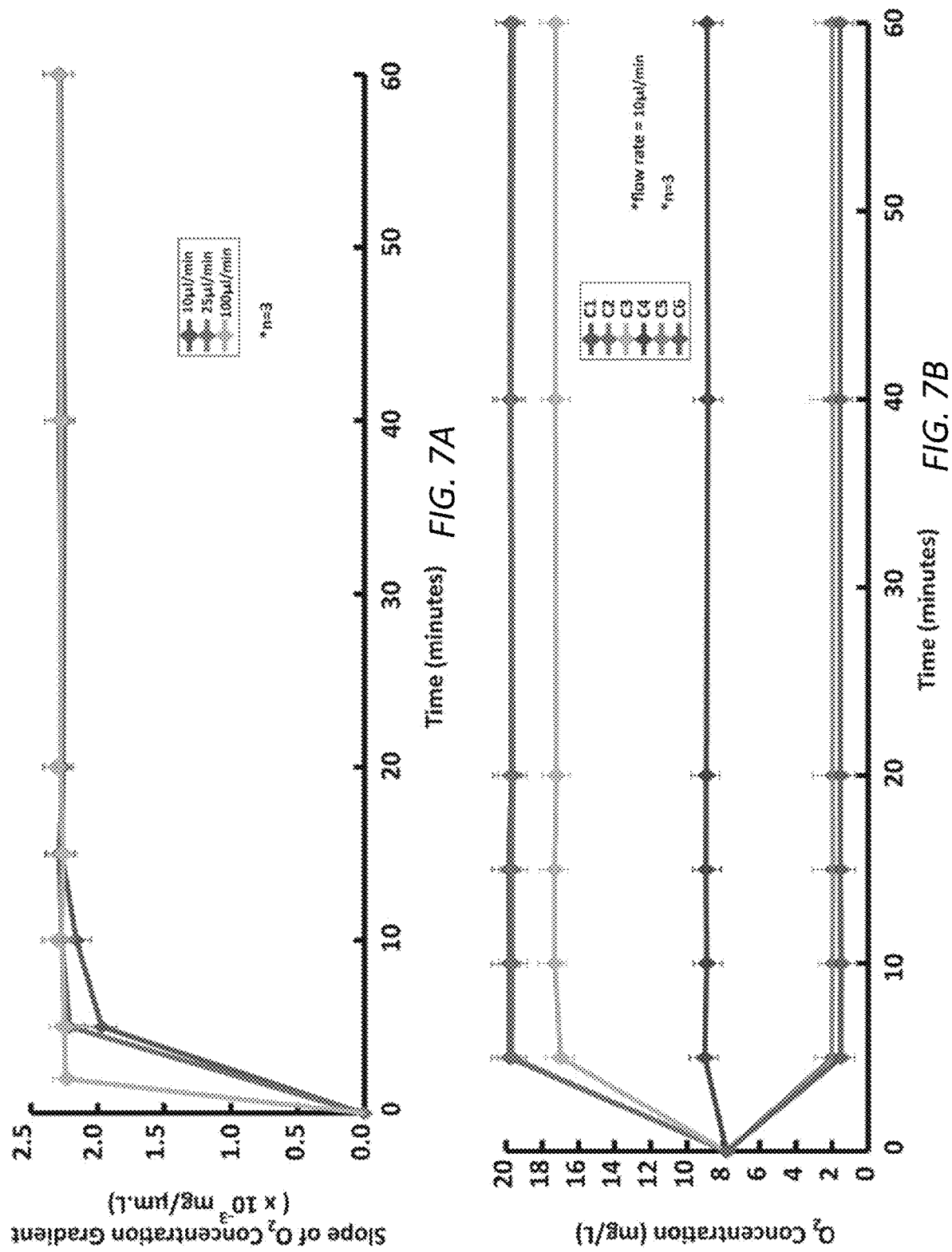

METHODS AND DEVICES FOR GENERATING CHEMICAL AND GASEOUS GRADIENTS IN MICROFLUIDIC PLATFORMS

CROSS REFERENCE TO RELATED APPLICATIONS

This application claims priority to, the benefit under 35 U.S.C. § 119 of, and incorporates by reference herein in its entirety U.S. Provisional Patent Application No. 62/582,394, filed Nov. 7, 2017, and entitled "Methods, Devices and Compositions Comprising Chemical and Gaseous Gradients."

STATEMENT REGARDING FEDERALLY-SPONSORED RESEARCH

This invention was made with government support under 1550976, awarded by National Science Foundation. The government has certain rights in the invention.

TECHNICAL FIELD

The present disclosure relates generally to microfluidic platforms/devices and, more particularly, to generating chemical and gaseous gradients in microfluidic platforms/devices.

BACKGROUND

Gaseous gradients are ubiquitous in biological systems. Hypoxic regions exist throughout the body and appropriate oxygen levels are maintained through a variety of physiological mechanisms such as reperfusion, angiogenesis, blood vessel dilation etc. Hypoxia plays a critical role in cancer progression and not only enhances the motility of cancer cells but also makes them resistant to chemo- and radiotherapies. Similarly, bacterial pathogens exhibit unique responses to aerobic and anaerobic conditions and modulate their behavior according to their local microenvironment. Thus, biomimetic re-creation of the gradients of dissolved gases in an in vitro environment is crucial to understand cell and disease functions. Similarly, generation of chemical gradients is critical to determine dose response of cells to drugs.

Few microfluidic strategies have been proposed to create gaseous gradients by infusing pure gases through a microchannel adjacent to the flow channel where the gas diffuses through a thin wall of PDMS (polydimethylsiloxane) and establishes the gradient. These strategies are complex, unsafe requiring availability of compressed gas tanks, and fail to offer a high spatial and temporal resolution of gradients.

Therefore, there is a long-felt but unresolved need for methods and devices to generate chemical and gaseous gradients in microfluidic platforms/devices.

BRIEF SUMMARY OF THE DISCLOSURE

Briefly described, and according to one embodiment, aspects of the present disclosure generally relate to methods, devices and compositions for making and using gradients of any desired gas (or multiple gases) within a microfluidic platform. In addition, parallel or opposing gradients of other agents, such as active agents, e.g., biological molecules or drugs, can be created in conjunction to the gaseous gradients. Cells can be cultured within the gradient chambers and the influence of gaseous or drug gradients or both can be evaluated, even in a resource limited setting.

The development of gaseous gradients can be achieved by bubbling pure oxygen (or another desired gas) through media of choice to increase the dissolved oxygen concentration. Final concentrations can be obtained by appropriate dilution of the stock solutions created by the bubbling method. Likewise, another gas such as nitrogen can be bubbled through media to create a solution lean in dissolved oxygen. In an aspect, these two solutions (oxygen rich and lean) are filled in gas-tight syringes, and introduced into the gradient generation platform to establish a gradient of oxygen across the channel. The specialized geometry of the device design allows this gradient creation purely based on diffusion even under laminar flow conditions. Overlapping chemical gradients can be created by mixing the desired chemical in one of the inlet streams. The detection of oxygen gradients can be achieved by incorporating a thin film of oxygen sensitive dye PtOEPK underneath the microchannels.

The PDMS polymer used to create the microfluidic devices is gas permeable. This characteristic of PDMS poses a challenge of the ambient gases to diffuse across PDMS and diminish the resolution of gradients. Disclosed herein are methods, devices and compositions comprising a thin glass coating on the inner walls of PDMS that prevents diffusion of gases across the channels. It also makes the PDMS based devices compatible for the utilization of organic solvents that usually tend to swell PDMS.

Disclosed herein are methods, systems and devices for creating dissolved gas gradients and detecting those gradients and changes to those gradients. Use of media with dissolved gas concentrations are contemplated by the present disclosure.

The combination of diffusion based gradient generation in conjunction with the 3-sided glass coating formation provides a novel strategy to establish gradients of any gas and/or chemical. Different designs can be developed for specific applications e.g. the single outlet design offers a continuous gradient while a multi-outlet design offers discrete concentrations of the dissolved gas within individual chambers. Also, the resolution of gradient in the multi-outlet device can be enhanced and customized by incorporating additional outlet chambers by increasing the number of split channel networks. These platforms can be utilized for a variety of applications including (i) convenient and quick testing of anticancer drug efficacies under hypoxic conditions, determination of dose responses for personalized medicine, basic research to understand cellular responses under hypoxic or hyperoxic conditions, bacteriological studies where carbondioxide plays a critical role by establishing carbondioxide gradients, or any other study requiring investigation of the effects of a specific gas or combination of gases and respective respnses to various drugs under such conditions.

In one embodiment, a microfluidic device, comprising: a substrate; and at least one reservoir bonded to the substrate, the at least one reservoir defining one or more channels, wherein at least a portion of an inner surface of the one or more channels is coated with a substance that inhibits diffusion of one or more components.

In one embodiment, a method of growing or maintaining cells under parallel or opposing gradients of gases, active agents, or both in a microfluidic device, comprising the steps of: introducing cells into the microfluidic device; providing a first cellular culture media composition comprising a first certain concentration of a first gas, a first active agent, or both; providing a second cellular culture media composition comprising a second certain concentration of a second gas, a second active agent, or both, wherein the second cellular culture media composition is different from the first cellular culture media composition; and allowing the cells to grow or be maintained in the microfluidic device, wherein the microfluidic device comprises: a substrate; and at least one reservoir bonded to the substrate, the at least one reservoir defining one or more channels, wherein at least a portion of an inner surface of the one or more channels is coated with a substance that inhibits diffusion of one or more components.

In one embodiment, a kit for growing or maintaining cells under parallel or opposing gradients of gases, active agents, or both in a microfluidic device, comprising: the microfluidic device, wherein the microfluidic device comprises: a substrate; and at least one reservoir bonded to the substrate, the at least one reservoir defining one or more channels, wherein at least a portion of an inner surface of the one or more channels is coated with a substance that inhibits diffusion of one or more components; and instructions for: introducing cells into the microfluidic device; providing a first cellular culture media composition comprising a first certain concentration of a first gas, a first active agent, or both; providing a second cellular culture media composition comprising a second certain concentration of a second gas, a second active agent, or both, wherein the second cellular culture media composition is different from the first cellular culture media composition; and allowing the cells to grow or be maintained in the microfluidic device.

According to one aspect of the present disclosure, the device, wherein the substrate comprises polydimethylsiloxane (PDMS), polymethylmythacrylate (PMMA), one or more thermoplastics, or glass, and wherein the one or more components comprise oxygen. Furthermore, the device, wherein the substance comprises polymeric silicon dioxide. Moreover, the device, further comprising an oxygen sensor. Further, the device, wherein the oxygen sensor comprises a platinum(II) octaethylporphyrin ketone (PtOEPK)-based sensor layer. Additionally, the device, further comprising a cell chamber connected to at least one of the one or more channels, wherein the oxygen sensor is located adjacent to the cell chamber. Also, the device, wherein a thin PDMS membrane separates the oxygen sensor from the cell chamber.

According to one aspect of the present disclosure, the method, wherein the substrate comprises polydimethylsiloxane (PDMS), polymethylmythacrylate (PMMA), one or more thermoplastics, or glass, and wherein the one or more components comprise oxygen. Furthermore, the method, wherein the substance comprises polymeric silicon dioxide. Moreover, the method, further comprising an oxygen sensor. Further, the method, wherein the oxygen sensor comprises a platinum(II) octaethylporphyrin ketone (PtOEPK)-based sensor layer. Additionally, the method, further comprising a cell chamber connected to at least one of the one or more channels, wherein the step of introducing cells into the microfluidic device further comprises the step of introducing the cells into the cell chamber. Also, the method, wherein the oxygen sensor is located adjacent to the cell chamber.

According to one aspect of the present disclosure, the method, wherein a thin PDMS membrane separates the oxygen sensor from the cell chamber. Furthermore, the method, wherein the first gas in oxygen. Moreover, the method, wherein the second gas is nitrogen or argon. Further, the method, wherein the cells comprise cancer cells. Additionally, the method, wherein the first and second active agents comprise anticancer drugs.

In one embodiment, a microfluidic device, comprising one or more channels and a polydimethylsiloxane (PDMS) substrate, wherein at least a portion of an inner surface of the one or more channels is coated with a substance that inhibits diffusion of one or more components. According to one aspect of the present disclosure, the device, wherein the coating inhibits diffusion of oxygen. Further, the device, wherein the coating comprises polymeric silicon dioxide. Moreover, the device, further comprising a gaseous of a chemical sensor. Furthermore, the device, wherein the sensor is an oxygen sensor. Additionally, the device, wherein the oxygen sensor is a layer of PtOEPK. Also, the device, wherein the sensor is located adjacent to a cell chamber. Moreover, the device, further comprising one or more cellular culture media compositions comprising defined concentrations of one or more gases and/or one or more active agents. Furthermore, the device, further comprising one or more cells.

In one embodiment, a kit comprising at least two cellular culture media compositions comprising a determined or particular concentration of one or more gases and/or one or more active agents. Generally, use in a device of a first cellular culture media composition having a certain concentration of a gas, an active agent or both and a second composition having a concentration of a gas, an active agent or both that is/are different from that of the first composition. Further, the use wherein the second composition comprises the same or a different cellular culture media.

In one embodiment, a method of making a microfluidic device, comprising making a microfluid device comprising one or more channels; and coating at least a portion of an interior surface of at least one channel. According to one aspect of the present disclosure, the method, further comprising providing one or more sensors to measure conditions within one or more channels of the device. Additionally, the method, wherein a sensor is an oxygen sensor. Also, the method, wherein the oxygen sensor comprises a platinum(II) octaethylporphyrin ketone (PtOEPK)-based sensor layer. Further, the method, wherein a platinum(II) octaethylporphyrin ketone (PtOEPK)-based sensor layer is formed adjacent to a cell chamber. Additionally, the method, wherein a thin PDMS membrane separates the sensor layer from the cell chamber.

In one embodiment, a method of creating linear and stable gaseous and/or active agent gradients having high spatial resolution, comprising simultaneously providing to a device disclosed herein a first cellular culture media composition having a certain concentration of a gas, an active agent or both and a second composition having a concentration of a gas, an active agent or both that is/are different from that of the first composition. According to one aspect of the present disclosure, the method, wherein the second composition comprises the same or a different cellular culture media.

In one embodiment, a method of growing or maintaining cells under parallel or opposing gradients of gases and/or active agents or both, comprising introducing cells into a disclosed microfluidic device disclosed herein, and providing a first cellular culture media composition having a certain concentration of a gas, an active agent or both and a second composition having a concentration of a gas, an active agent or both that is/are different from that of the first composition; and allowing the cells or grow or be maintained in the disclosed device. According to one aspect of the present disclosure, the method, wherein the second composition may comprise the same or a different cellular culture media. Furthermore, the method, wherein the cells may reside in the disclosed device in a cell chamber. Moreover, the method, wherein the cells are grown or maintained under a parallel gradient. Additionally, the method, wherein the cells are grown or maintained under an opposing gradient.

In one embodiment, a method for investigating a cellular response to one or more particular physiological states, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring one or more characteristics of the treated cells, and comparing the one or more characteristics of the treated cells to the same characteristics of untreated cells. Also, the method, wherein the physiological state is oxygen.

In one embodiment, a method of investigating cellular migration in response to one or more physiological states, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring the migration of the treated cells, and comparing the migration of the treated cells to the migration of untreated cells. According to one aspect of the present disclosure, the method, wherein the physiological state is oxygen.

In one embodiment, a method of investigating reaction kinetics in cells in response to one or more physiological states, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring the migration of the treated cells, and comparing the migration of the treated cells to the migration of untreated cells. According to one aspect of the present disclosure, the method, wherein the device and or compositions have been purged with nitrogen gas or argon gas.

In one embodiment, a kit comprising a disclosed microfluidic device. According to one aspect of the present disclosure, the kit, further comprising one or more compositions comprising cellular culture media comprising a particular concentration of one or more gases, one or more active agents, or both. Moreover, the kit, further comprising cells. Additionally, the kit, further comprising printed instructions or a computer link to instructions for using the components of the kit.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 7 (consisting of FIGS. 7A and 7B) illustrates exemplary oxygen concentrations/gradients, according to one embodiment of the present disclosure.

DETAILED DESCRIPTION

Figure 1A:
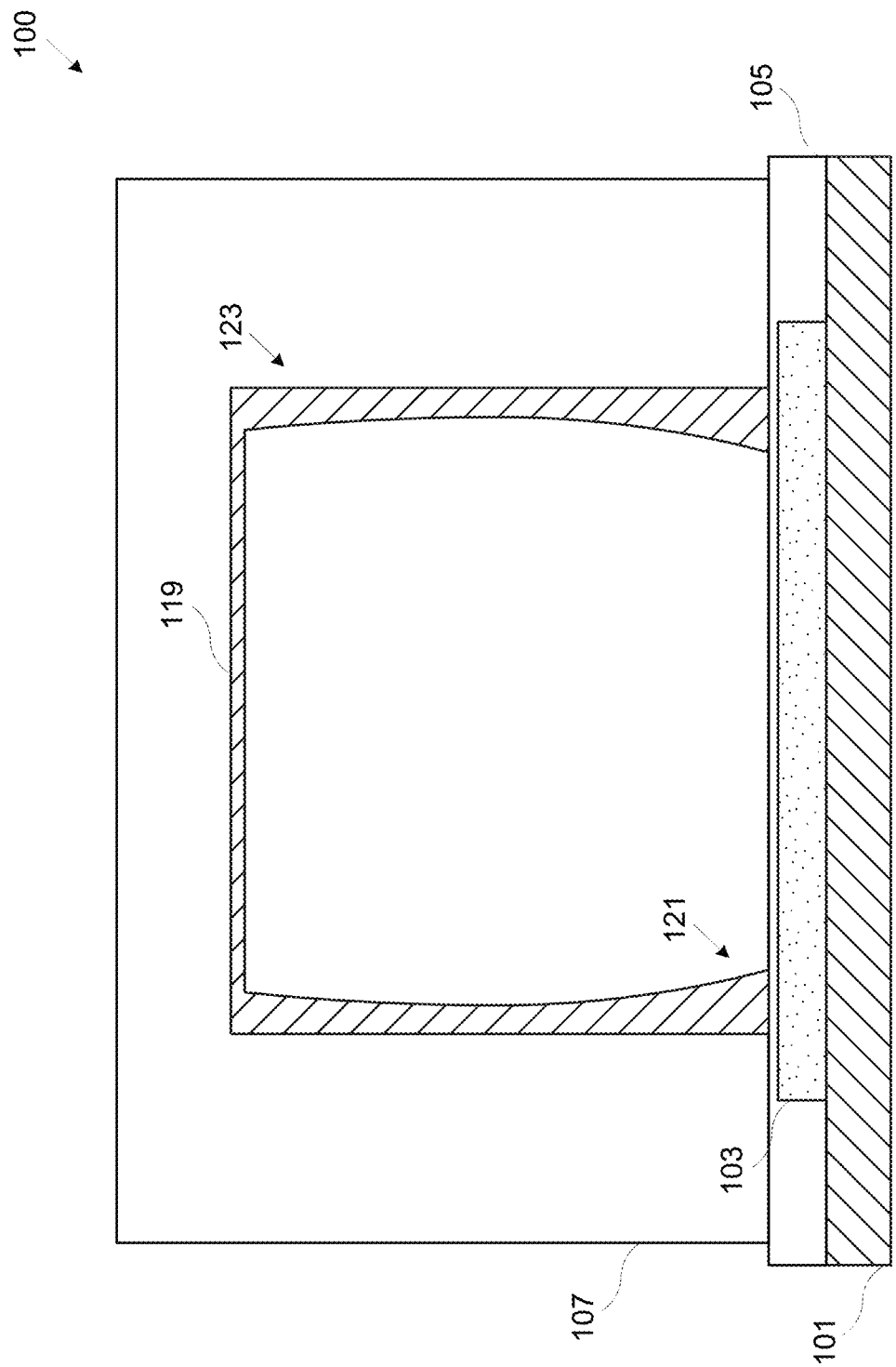
FIG. 1 (consisting of FIGS. 1A-1D) illustrates an exemplary microfluidic device, according to one embodiment of the present disclosure.

For the purpose of promoting an understanding of the principles of the present disclosure, reference will now be made to the embodiments illustrated in the drawings and specific language will be used to describe the same. The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Briefly described, and according to one embodiment, aspects of the present disclosure generally relate to methods, devices and compositions for making and using gradients of any desired gas (or multiple gases) within a microfluidic platform. In addition, parallel or opposing gradients of other agents, such as active agents, e.g., biological molecules or drugs, can be created in conjunction to the gaseous gradients. Cells can be cultured within the gradient chambers and the influence of gaseous or drug gradients or both can be evaluated, even in a resource limited setting.

The development of gaseous gradients can be achieved by bubbling pure oxygen (or another desired gas) through media of choice to increase the dissolved oxygen concentration. Final concentrations can be obtained by appropriate dilution of the stock solutions created by the bubbling method. Likewise, another gas such as nitrogen can be bubbled through media to create a solution lean in dissolved oxygen. In an aspect, these two solutions (oxygen rich and lean) are filled in gas-tight syringes, and introduced into the gradient generation platform to establish a gradient of oxygen across the channel. The specialized geometry of the device design allows this gradient creation purely based on diffusion even under laminar flow conditions. Overlapping chemical gradients can be created by mixing the desired chemical in one of the inlet streams. The detection of oxygen gradients can be achieved by incorporating a thin film of oxygen sensitive dye PtOEPK underneath the microchannels.

The PDMS polymer used to create the microfluidic devices is gas permeable. This characteristic of PDMS poses a challenge of the ambient gases to diffuse across PDMS and diminish the resolution of gradients. Disclosed herein are methods, devices and compositions comprising a thin glass coating on the inner walls of PDMS that prevents diffusion of gases across the channels. It also makes the PDMS based devices compatible for the utilization of organic solvents that usually tend to swell PDMS.

Disclosed herein are methods, systems and devices for creating dissolved gas gradients and detecting those gradients and changes to those gradients. Use of media with dissolved gas concentrations are contemplated by the present disclosure.

The combination of diffusion based gradient generation in conjunction with the 3-sided glass coating formation provides a novel strategy to establish gradients of any gas and/or chemical. Different designs can be developed for specific applications e.g. the single outlet design offers a continuous gradient while a multi-outlet design offers discrete concentrations of the dissolved gas within individual chambers. Also, the resolution of gradient in the multi-outlet device can be enhanced and customized by incorporating additional outlet chambers by increasing the number of split channel networks. These platforms can be utilized for a variety of applications including (i) convenient and quick testing of anticancer drug efficacies under hypoxic conditions, determination of dose responses for personalized medicine, basic research to understand cellular responses under hypoxic or hyperoxic conditions, bacteriological studies where carbondioxide plays a critical role by establishing carbondioxide gradients, or any other study requiring investigation of the effects of a specific gas or combination of gases and respective responses to various drugs under such conditions.

Referring now to the figures, for the purposes of example and explanation of the fundamental processes and components of the present disclosure, reference is made to FIG. 1 (consisting of FIGS. 1A-1D), which illustrates an exemplary, high-level overview of one embodiment of the disclosed microfluidic device 100. As will be understood and appreciated, the exemplary microfluidic device 100 shown in FIG. 1 represents merely one approach or embodiment of the present system, and other aspects are used according to various embodiments of the present system.

Figure 1B:
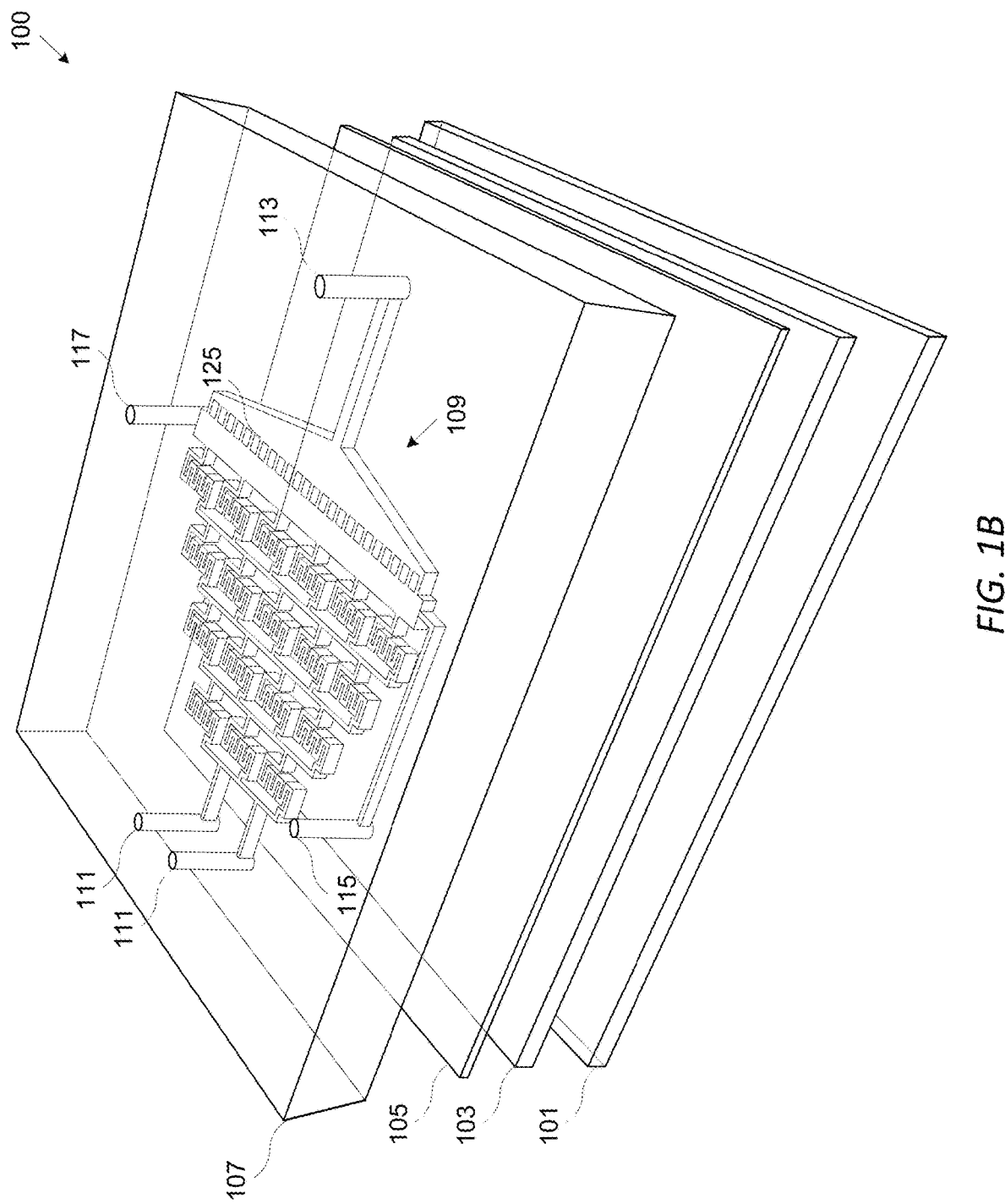
Figure 1C:
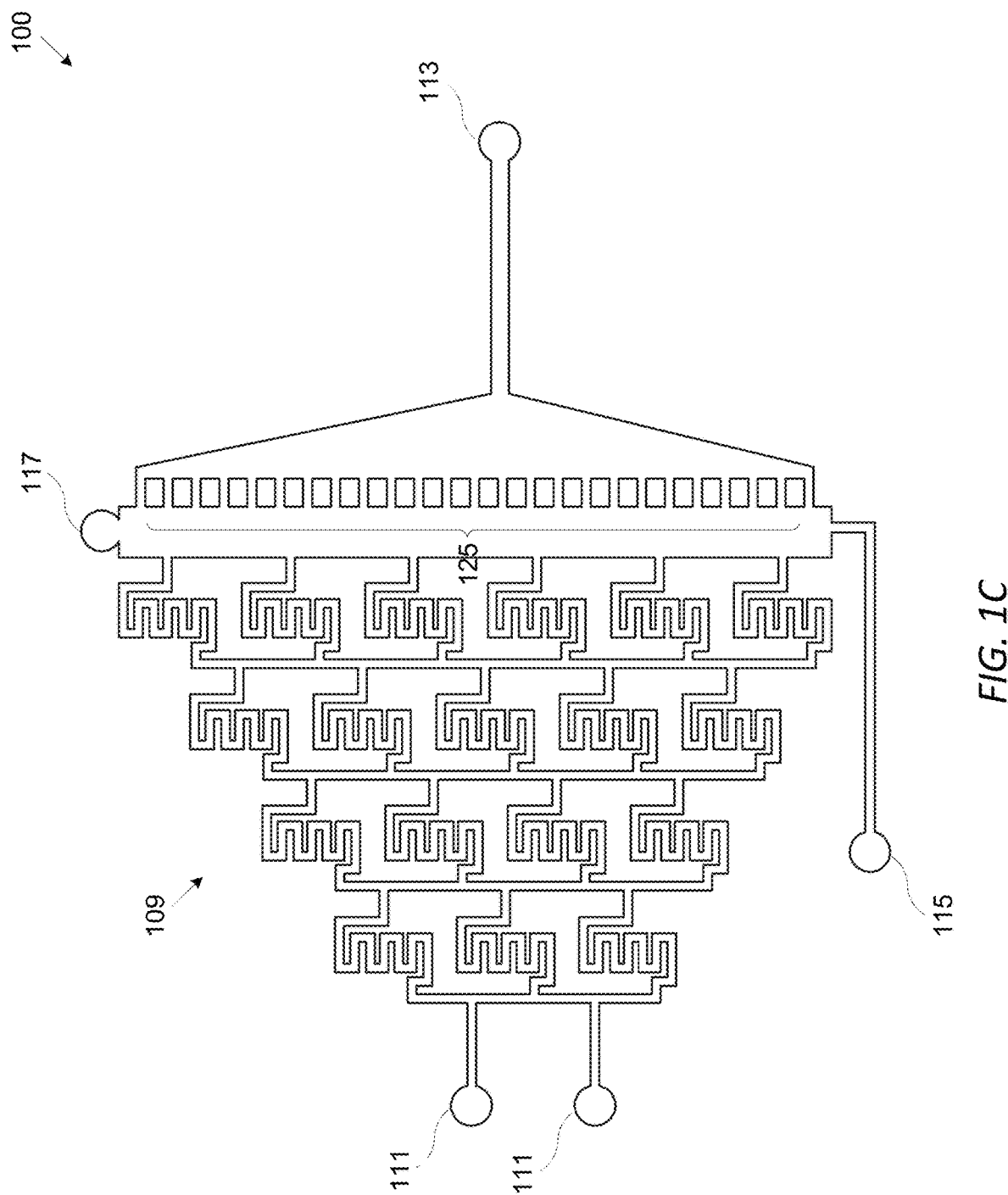
Figure 1D:
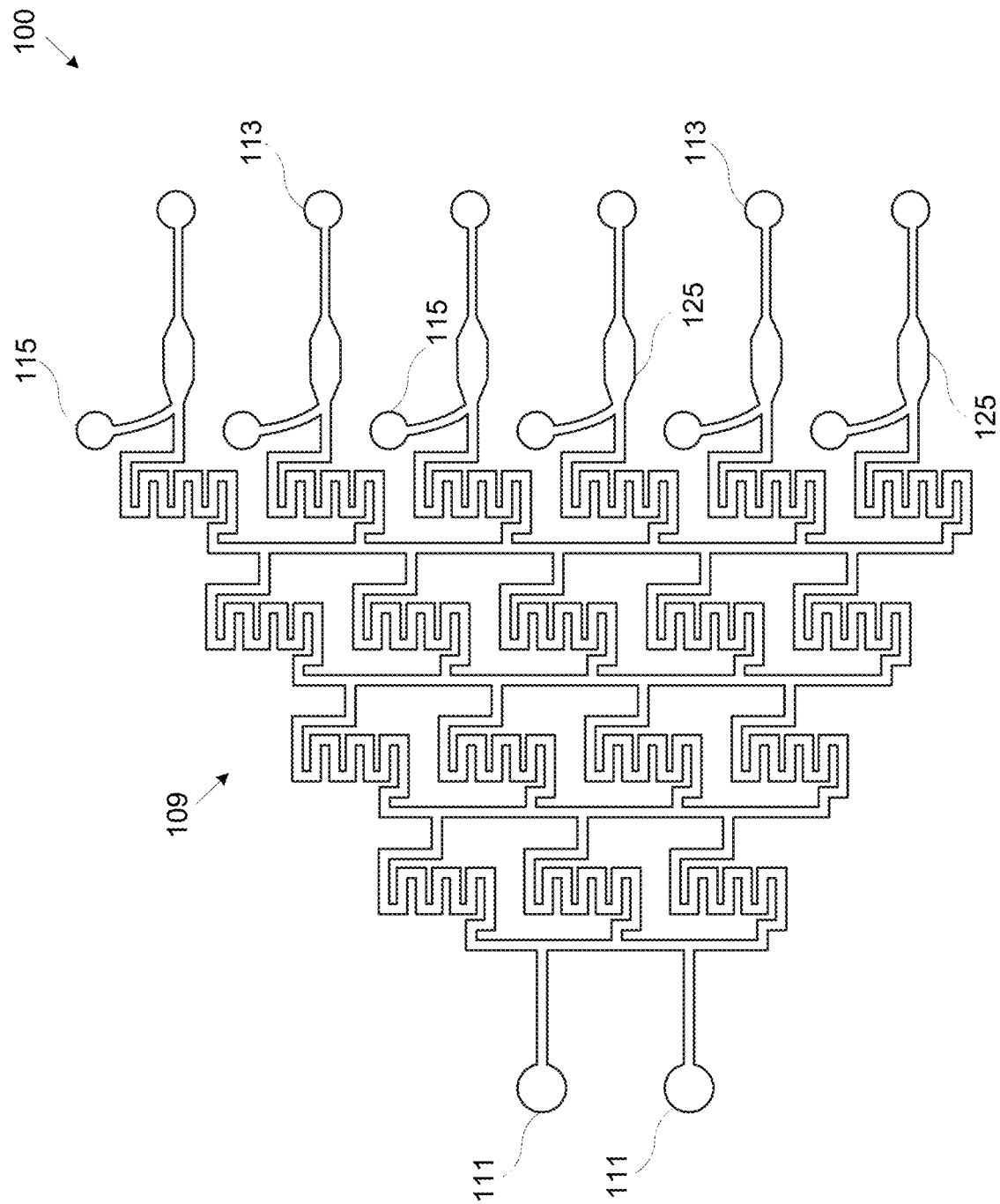

Generally, FIG. 1A illustrates an exemplary cross-section view of a microfluidic device 100; FIG. 1B illustrates an exemplary exploded view of a microfluidic device 100; FIG. 1C illustrates an exemplary top view of a microfluidic device 100; and FIG. 1D illustrates an alternative exemplary top view of a microfluidic device 100. In various embodiments, the exemplary microfluidic device 100 comprises one or more layers 101, 103, 105, and 107, wherein layer 107 defines a reservoir 109 with one or more media inlets 111, media outlets 113, cell inlets 115, cell outlets 117, and cell chambers 125. In one embodiment, layer 101 comprises a microscope slide (e.g., glass, etc.); layer 103 comprises PtOEPK/PS; layer 105 comprises a thin PDMS membrane; and layer 107 comprises PDMS. Generally, in one embodiment, the channels have a sol-gel/glass coating 119 on three interior sides, a wider bottom edge 121, and a thinner top edge 123.

In one non-limiting example, a fabricated single-reservoir device 100 with channel dimensions of 250 μm (w)×100 μm (h) and the length of each serpentine segment is approximately 7.6 mm. Generally, the blocks, separated by 187.5 μm gap, are placed as support structures to prevent the top PDMS surface from collapsing. In an alternate embodiment, a fabricated multiple outlet device 100 with channel dimensions of 200 μm (w)×100 μm and the same length of each serpentine segment as the single-reservoir device 100. In various embodiments, the exterior dimensions of the device 100 may be approximately 1.6 cm by 2.2 cm, wherein the channels occupy 1.46 cm of the 2.2 cm.

Now referring to FIG. 2 (consisting of FIGS. 2A-2F), exemplary details regarding the disclosed glass coating (for channels) are shown according to one embodiment of the present disclosure. Generally, FIG. 2A illustrates Z-stack fluorescent image of the inverted channel with 3-sided glass coating. 1 μm fluorescent polystyrene beads were mixed in the sol-gel solution prior to coating formation to facilitate the presence of glass coating; FIG. 2B illustrates high resolution 3D phase-contrast image of the 3-sided coated channel at optimal conditions showing glass-coating (~7 μm thick) on walls with no unpolymerized spaces and minimal crack formation taken with an Olympus laser confocal surface profilometer; FIG. 2C graphically represents variation in average glass coating thickness across different temperatures and times; FIG. 2D illustrates glass coating with unpolymerized spaces, typical at lower temperatures and reaction times; and FIG. 2E illustrates with FIG. 2F corresponding mean intensity curves showing leeching profile comparison of coated versus uncoated channels using 1 μM rhodamine B solution in DI water.

Figures 3A, 3B:
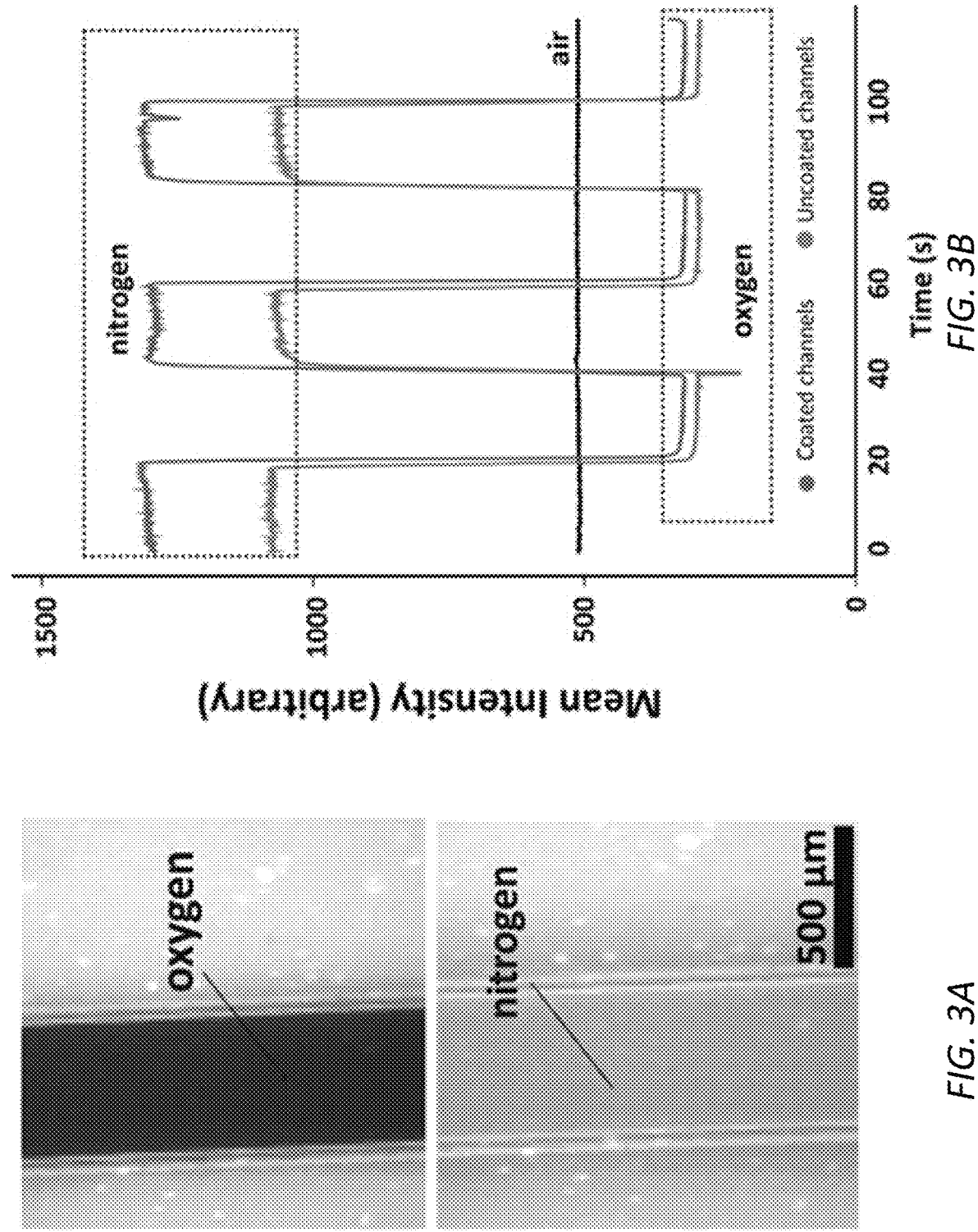
FIG. 3 (consisting of FIGS. 3A-3D) illustrates differences between coated and uncoated channels, according to one embodiment of the present disclosure.

Referring now to FIG. 3 (consisting of FIGS. 3A-3D), exemplary differences between coated and uncoated channels are shown according to one embodiment of the present disclosure. Generally, FIG. 3A illustrates a change in intensity of the underlying PtOEPK dye when exposed to gaseous nitrogen (bottom) and oxygen (top) gas—gases were introduced into the channels by connecting regulated compressed tanks of respective gases through tygon tubing; FIG. 3B graphically represents dynamic sensing ability and comparison of coated versus uncoated channels (air being considered baseline) after periodic introduction of oxygen and nitrogen gas; FIG. 3C graphically represents a calibration curve for gaseous oxygen detection of coated and uncoated channels; and FIG. 3D graphically represents calibration curve for dissolved oxygen detection illustrating the relative chemiluminescent intensity of PtOEPK corresponding to different concentrations of dissolved oxygen in DI water.

Now referring to FIG. 4, exemplary oxygen gradients are shown according to one embodiment of the present disclosure. Generally, FIGS. 4A and 4B illustrate (i) COMSOL simulated oxygen gradient profile in single-reservoir device at 1 μL/min (ii) oxygen concentration gradient across the reservoir detected by PtOEPK luminescence, wherein the gradient was established by flowing 19.9 mg/L and 0.1 mg/L oxygenated water at 10 μL/min flowrate, and (iii) profile of oxygen concentration gradient near the outlet of single reservoir device, showing increasing slope of gradient with increasing flow rates (flowing 19.9 mg/L and 0.1 mg/L DO water at 25 μL/min and 100 μL/min)—though overall gradient across reservoir is the same throughout, the oxygen profile tends to equilibrate by the time it approaches the outlet due to the very long residence time of 49 minutes; FIG. 4C graphically represents a concentration plot comparison of COMSOL and experimental data across the single reservoir as denoted in (ii); FIG. 4D graphically represents a concentration plot illustrating progressive trend in the slope of gradient (near the outlet of single reservoir device as denoted in (iii) with respect to the flow rate and comparison with COMSOL data; FIG. 4E illustrates unit concentration of oxygen formed in each chamber of the multiple outlet device (both COMSOL and experimental); and FIG. 4F graphically represents a comparison of actual versus predicted (COMSOL) concentrations within individual chambers of the multiple outlet device.

Figure 5B:
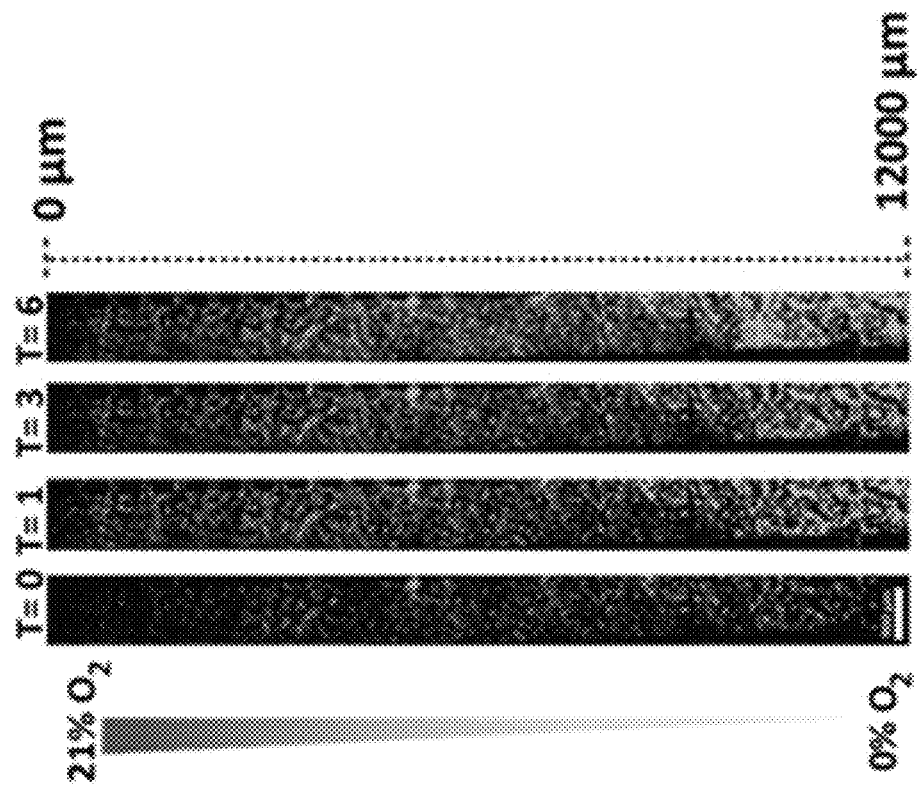
FIG. 5 (consisting of FIGS. 5A-5E) illustrates exemplary ER stress, according to one embodiment of the present disclosure.
Figure 5A:
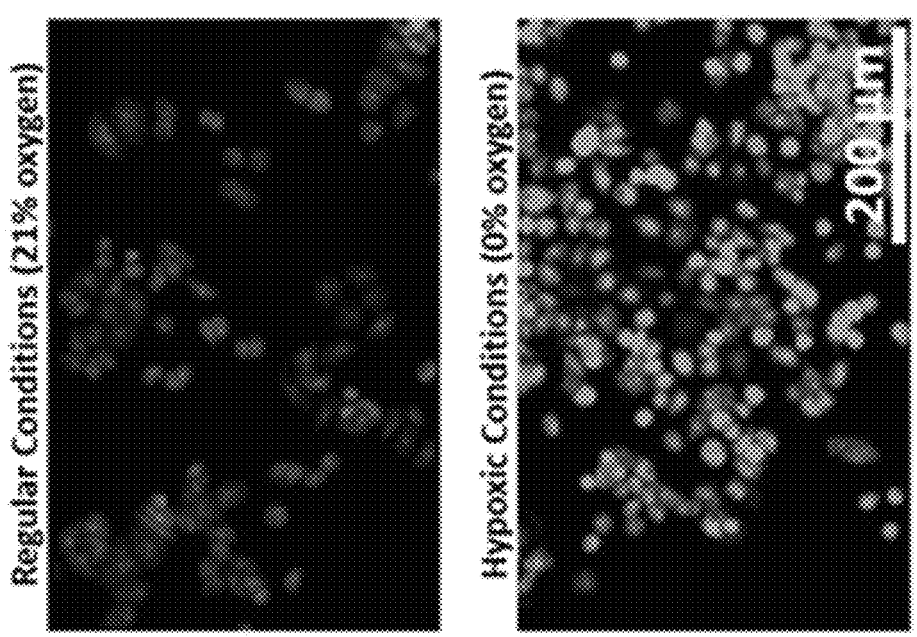

Referring now to FIG. 5 (consisting of FIGS. 5A-5E), exemplary ER stress is shown according to one embodiment of the present disclosure. Generally, FIG. 5A illustrates a comparison of ER stress of MDA-MB-468 cells via Thioflavin T fluorescence under normal and hypoxic conditions, showing elevated ER stress levels in hypoxia; FIG. 5B illustrates ER stress across region I in single-outlet device with oxygen gradient generated at a flow rate of 1 μL/min at 0 hr, 1 hr, 3 hr and 6 hr—the fluorescence increases under oxidative stress resulting in progressively higher fluorescence towards the hypoxic edge of region I of the single-outlet device and with time; FIG. 5C graphically represents a fluorescence trend of MDA-MB-468 cells across region I, illustrating gradual and significant increase in ER stress from baseline due to oxidative stress at different time periods, wherein nearly a 4-fold increase is noticeable in the most hypoxic region; and FIGS. 5D and 5E illustrate a viability analysis of MCF-12A under hypoxia gradient established within the multiple-outlet device, wherein incubating cells for 6 hours under oxygen gradient illustrated increasing mortality with reducing oxygen levels (the concentration values labeled for each panel were experimentally derived).

Figure 6:
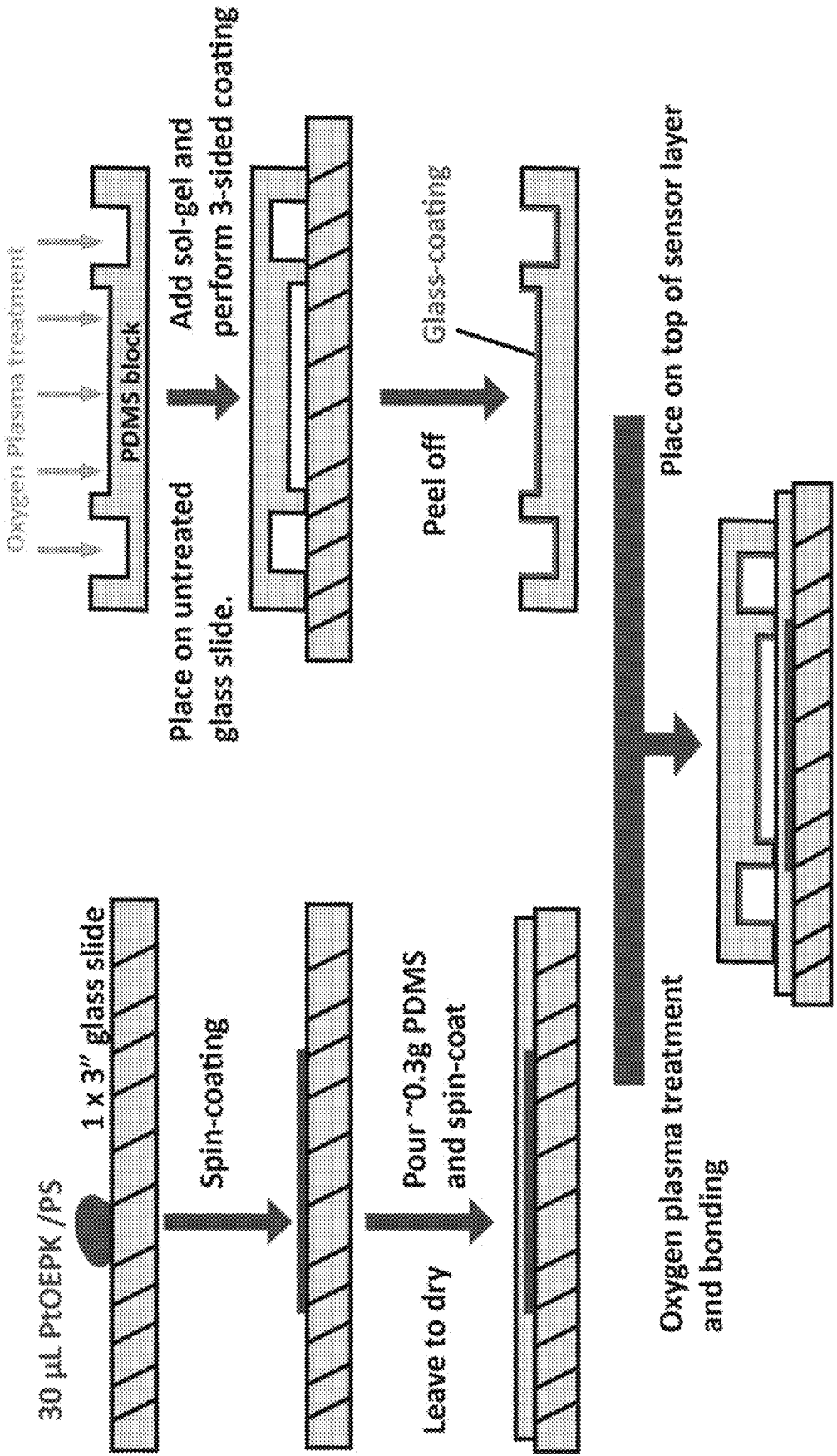
FIG. 6 illustrates an exemplary device fabrication process, according to one embodiment of the present disclosure.

Now referring to FIG. 6, an exemplary device fabrication process is shown according to one embodiment of the present disclosure. As will be understood by one having ordinary skill in the art, the steps and processes shown in FIG. 6 (and those of all other flowcharts, sequence diagrams, and processes shown and/or described herein) may operate concurrently and continuously, are generally asynchronous and independent, and are not necessarily performed in the order shown.

Referring now to FIG. 7 (consisting of FIGS. 7A and 7B), exemplary oxygen concentrations/gradients are shown according to one embodiment of the present disclosure. Generally, FIG. 7A graphically represents the slope of the gradient across the reservoir in the single reservoir device over time, at different flow rates, which shows the time required to formed the respective gradients and that the generated oxygen gradients are stable over lengthy time periods; and FIG. 7B graphically represents the stability of the unit concentrations of oxygen being formed in each of the respective chambers or outlets inside the multiple-outlet device, also exhibiting stability over a 1-hour time period.

Figures 8A, 8B:
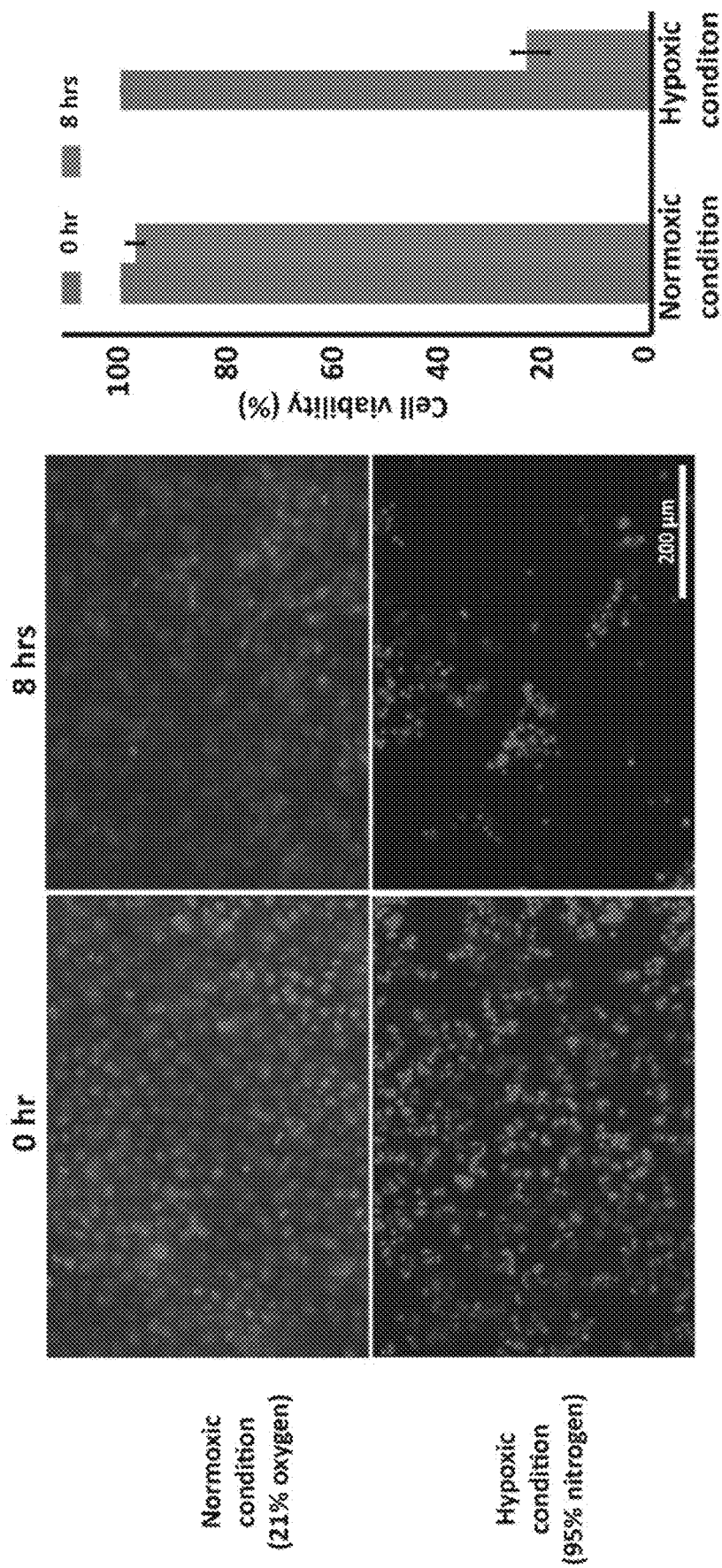
FIG. 8 (consisting of FIGS. 8A and 8B) illustrates viability analysis of cells, according to one embodiment of the present disclosure.

Now referring to FIG. 8 (consisting of FIGS. 8A and 8B), viability analysis of MCF-12A cells in a 96-well plate for normal and hypoxic condition is shown according to one embodiment of the present disclosure. Generally, FIG. 8A illustrates micrographs of cells stained with CMTPX for cytoplasm and Hoechst for nuclei; and FIG. 8B graphically represents quantitative analysis of cell viability showing ~80% decrease in cell viability under hypoxic condition.

Figure 9:
FIG. 9 illustrates cells seeded in exemplary device, according to one embodiment of the present disclosure.

Referring now to FIG. 9, a phase-image of MCF-12A cells being seeded in one of the chambers or outlets in multiple-outlet device is shown according to one embodiment of the present disclosure.

Exemplary Embodiments

Hypoxic regions exist within most solid tumors and often lead to altered cellular metabolism, increased motility, and drug resistance. Simultaneous generation and detection of gaseous gradients in vitro is challenging and biomimetic hypoxic conditions are yet to be replicated due to low spatiotemporal resolution and poor longevity of the gradients generated utilizing microfluidic techniques. Disclosed herein are methods, devices and compositions for producing gradients of dissolved oxygen within a robust lab-on-a-chip platform. A thin 3-sided glass coating on the inner channel walls prevented multi-directional diffusion of ambient oxygen across the polydimethylsiloxane (PDMS) substrate. In one embodiment, the substrate comprises polymethylmythacrylate (PMMA), a thermoplastic, or glass. Linear and stable gradients with high spatial resolution were generated by introducing pre-gassed media into the passive gradient generating channel network. An underlying platinum (ii) octaethlporphyrin ketone PtOEPK based sensor layer allowed real-time detection of the dissolved oxygen. Viability analysis of normal mammary epithelial cells (MCF-12A) cultured within the gradient chamber revealed 88% mortality under hypoxic conditions after an 8-hour incubation period. The unique ability to establish parallel or opposing gradients of gases and active agents, e.g., chemicals offers potential for a wide range of applications in novel therapeutic development, metastasis, and biotechnology.

Oxygen homeostasis is critical for the existence of multicellular organisms. While oxygen deficiency or hypoxia can result in pathological conditions such as ischemia and tumorigenesis, elevated oxygen levels (hyperopia) can lead to generation of reactive oxygen species and free-radicals[4]. During cancer progression, rapid growth of tumor lesions lead to internal hypoxic conditions, which in turn initiates angiogenesis, followed by tumor cell invasion into healthy tissues and eventual metastasis. The blood vessels generated from pathological angiogenesis are highly disorganized and morphologically irregular, impeding nutrient supply and metabolite clearance and eventually culminating in acquiring drug resistance.

In vitro generation as well as detection of dissolved oxygen (DO) is crucial for a wide range of applications including therapeutic development and understanding of disease functions. Typically, exploration of cellular functions under controlled oxygen environments are conducted using specialized culture chambers (e.g. $O_2$ incubators). Unfortunately, such systems can only maintain a singular oxygen concentration, significantly varying from the actual physiological conditions where DO gradients normally exist within tissues. To address this, bi-compartmental open-well cell culture devices, similar to Boyden chambers, have been developed where oxygen (and nitrogen), flowing in the lower compartment, diffuses through a polydimethylsiloxane (PDMS) barrier into the upper compartment where the cells are seeded. The introduction and evolution of microfluidic devices have further improved this scenario, offering the ability to rapidly generate a range of oxygen tension profiles in vitro and investigate cellular responses under oxygen gradients. These utilize either multiple gas inlets to establish DO gradients or chemical quenchers such as $Na_2SO_3$ that deplete oxygen from the media. Unfortunately, the requirement of continuous gas flow not only introduces potential risks of bubble formation and media evaporation, but also limits the portability of experimental setups as they are confined to the proximity of compressed gas tanks. On the other hand, chemical quenchers are cytotoxic and are often undesirable while investigating therapeutic-effects of drugs under hypoxic conditions. Both approaches are only able to generate DO gradients with low-to-moderate spatial resolution. Increasing the number of gas inlets may improve the spatial resolution, but at the cost of significantly multiplying the aforementioned risks and disadvantages involved.

In addition to gradient generation, the ability to detect dissolved DO levels in real-time is desirable to validate both reproducibility and overall experimental outcome. Detection of DO is achieved either electrochemically through amperometric Clark-type electrodes or optically via oxygen-sensitive dyes. Though extensively used in commercial gas detectors, the macroscale size of the electrode, along with low sensitivity, long response time, and analyte depletion and fouling by organic fluids restricts its usage in microfluidic oxygen detection. Optical-based detection utilizes a polymer-encapsulated luminescent dye, such as phosphorescent metalloporphyrin complexes and fluorescent organoruthenium complexes. DO content is proportional to the quenching of dye luminescence, thus enabling non-invasive and dynamic sensing of oxygen. Though, nanoparticles of such dyes have recently been synthesized, potential leeching and subsequent cytotoxicity issues have limited their adaptation for biological applications.

Disclosed herein are methods, devices and compositions for generating and detecting stable biomimetic oxygen gradients with high spatial resolution. Simultaneous infusion of $O_2$-rich and $O_2$-depleted media (pre-gassed) allowed generation of stable DO gradients by utilizing the microfluidic split-and-recombine strategy, as seen with chemical gradients. Disclosed devices comprising a 3-sided glass-like coating within the PDMS microchannel prevents multi-directional diffusion of oxygen and maintains a spatially as well as temporally stable gradient. Thus, devices comprising of gas inlets and media compositions comprising chemical quenchers are not contemplated by the disclosed devices and media compositions.

In an aspect, a disclosed device comprises 0, 1 or 2 gas inlets. In an aspect, a disclosed device comprises 2 gas inlets. In an aspect, a disclosed device comprises 1 gas inlet. In an aspect, a disclosed device comprises 0 (zero or no) gas inlets. In an aspect, a media composition comprises one or more chemical quenchers of oxygen or other gases. In an aspect, a media composition comprises no chemical quenchers of oxygen or other gases. In an aspect, a media composition comprises no $Na_2SO_3$.

In an aspect, a disclosed device comprises real-time detection of DO by a layer of platinum(ii)octaethylporphyrin ketone embedded in a polystyrene matrix (PtOEPK/PS) underlying the gradient channel (FIG. 1A). A thin PDMS membrane separates the sensor-layer from cell chamber to prevent any dye mediated toxicity. Computational modelling using COMSOL Multiphysics was performed to verify gradient formation and device optimization. Two basic designs were used. Primary gradient generation was conducted inside a single-reservoir type device, similar to the microfluidic devices first established by Jeon and colleagues to generate intrinsic chemical gradients, where all the channels (250 μm wide) unite and converge into a single outlet (FIGS. 1B and 1C). To further broaden the versatility of the gradient system, a multiple-outlet device was designed (FIG. 1D). Here, the individual concentration streams remain separated to explore the possibility of forming unit concentrations of DO in each outlet. Among numerous potential applications, the proof-of-concept functionality of this platform was demonstrated as shown by Examples herein. Disclosed herein are methods, devices and compositions having convenience and versatility to establish a wide range of gaseous gradients under biomimetic conditions. Disclosed methods, devices and compositions provide novel, feasible, and reproducible ways to study cell functions under hypoxic, hyperoxic, or other gaseous gradient conditions.

Disclosed herein are devices, including microfluidic devices comprising one or more channels. In an aspect, a microfluidic device comprises one or more channels and a polydimethylsiloxane (PDMS) substrate, wherein at least a portion of an inner wall of the one or more channels is coated with a substance that inhibits diffusion of one or more gases. For example, a channel coating may comprise a glass-like substance. For example, a coating may comprise a silicon dioxide polymer. A coating may cover at least a portion of the interior surface of a channel. A coating may cover at least a portion of the interior surface of a channel; including but not limited to the bottom surface, one side surface, two side surfaces, a top surface, or one or more of the surfaces in all or a portion of the length of the channel. In an aspect, a coating may cover at least the bottom surface and two side surfaces in a portion of the length of the channel. A coating may comprise a polymer and may further comprise particles, such as detection particles, for example, fluorescent polystyrene beads. In an aspect, a coating may be provided that inhibits diffusion or transmission of substances other than gases, such as liquids or solids. In one embodiment, the substrate comprises polymethylmythacrylate (PMMA), a thermoplastic, or glass.

A disclosed device may comprise one or more sensors. For example, a sensor may be reactive to environmental or chemical characteristics of media or cells within a device. For example, a sensor may be a temperature sensor, a chemical sensor, a gas sensor, a light sensor, or any other sensor known to those of skill in the art for measuring environmental, compositional or cellular characteristics. In an aspect, a disclosed device comprises an oxygen sensor. In an aspect, an oxygen sensor comprises a platinum(II) octaethylporphyrin ketone (PtOEPK)-based sensor layer. For example, a PtOEPK-based sensor layer may reside under an area in a disclosed device wherein cells can or do reside, e.g., a cell chamber. A thin PDMS membrane may separate the sensor layer from a cell chamber to aid in preventing dye-mediated toxicity to the cells. For example, a PtOEPK-based sensor layer may reside under a channel in which a gas gradient is present. A PtOEPK-based sensor layer is useful in devices and methods wherein real-time detection of dissolved oxygen is desired.

Disclosed herein are compositions comprising cellular culture media comprising defined concentration of gases and/or active agents. As used herein "cellular media" means the media in which cells can be grown, maintained or stored under in vitro or in vivo conditions, as is commonly understood by those of skill in the relevant art. Such media is available from commercial sources, and maybe modified for specific cell types. As used herein "cells" means any cells that can be grown or maintained in cell culture media, including but not limited to, cells obtained by biopsy or removal from a multicellular organisms or organs or tissues, single cellular organisms, eukaryotic cells, prokaryotic cells, archea, protists, plant cells, animal cells, whether free-living or in colonies, cells that are short-lived or long-lived, cells that are transformed, cells that reproduce often or not at all, and cells that synthetically produced or are altered from a biologically known cell.

Disclosed herein is a composition comprising cellular culture media comprising a determined or particular concentration of one or more dissolved gases. For example, a composition comprises cellular culture media comprising a determined or particular concentration of dissolved oxygen. For example, a composition comprises cellular culture media comprising a determined or particular concentration of dissolved oxygen and a determined or particular concentration of carbon dioxide.

Disclosed herein is a composition comprising cellular culture media comprising a determined or particular concentration of one or more active agents. As used herein, an "active agent" is any compound, molecule or biological molecule, e.g., a protein, that is capable of activity in a biological or chemical environment. Commonly known active agents include, but are not limited to, drugs, chemical compounds, biologics, chemical elements, vitamins, antibiotics, chemotherapeutic agents, herbicides, pesticides, growth enhancers, growth retardants, and biosimilar molecules.

Disclosed herein is a composition comprising cellular culture media comprising a determined or particular concentration of one or more gases and one or more active agents. For example, a composition comprises cellular culture media comprising a determined or particular concentration of dissolved oxygen and a chemotherapeutic agent. Disclosed herein is a kit comprising at least two cellular culture media compositions comprising a determined or particular concentration of one or more gases and/or one or more active agents.

In methods of use of one or more disclosed compositions in a disclosed device, a first cellular culture media composition having a certain concentration of a gas, an active agent or both is used with a second composition having a concentration of a gas, an active agent or both that is/are different from that of the first composition. The second composition may comprise the same or a different cellular culture media. For example, simultaneous infusion into a disclosed device of a first cellular culture media composition having a high concentration of dissolved oxygen and a second cellular culture media composition having a low concentration of dissolved oxygen is used to generate stable dissolved oxygen gradiants in devices disclosed herein. For example, simultaneous infusion into a disclosed device of a first cellular culture media composition having a high concentration of dissolved oxygen and a low concentration of an active agent and a second cellular culture media composition having a low concentration of dissolved oxygen and a high concentration of the active agent is used to generate stable and opposing dissolved oxygen gradients and the active agent gradients in devices disclosed herein. For example, simultaneous infusion into a disclosed device of a first cellular culture media composition having a high concentration of dissolved oxygen and a high concentration of an active agent and a second cellular culture media composition having a low concentration of dissolved oxygen and a low concentration of the active agent is used to generate stable and parallel dissolved oxygen gradients and the active agent gradients in devices disclosed herein.

Disclosed herein are methods of making a microfluidic device disclosed herein, comprising making a microfluid device comprising one or more channels; and coating at least a portion of an interior surface of at least one channel. A method further comprises providing one or more sensors. In an aspect, a sensor comprises an oxygen sensor. In an aspect, an oxygen sensor comprises a platinum(II) octaethylporphyrin ketone (PtOEPK)-based sensor layer. In an aspect, the platinum(II) octaethylporphyrin ketone (PtOEPK)-based sensor layer is adjacent to a cell chamber. A thin PDMS membrane may separate the sensor layer from the cell chamber.

Disclosed herein are methods of creating linear and stable gaseous and/or active agent gradients having high spatial resolution, comprising simultaneously providing to a device disclosed herein a first cellular culture media composition having a certain concentration of a gas, an active agent or both and a second composition having a concentration of a gas, an active agent or both that is/are different from that of the first composition. The second composition may comprise the same or a different cellular culture media.

Disclosed herein are methods of growing or maintaining cells under parallel or opposing gradients of gases and/or active agents or both, comprising introducing cells into a disclosed microfluidic device disclosed herein, and providing a first cellular culture media composition having a certain concentration of a gas, an active agent or both and a second composition having a concentration of a gas, an active agent or both that is/are different from that of the first composition, and allowing the cells or grow or be maintained in the disclosed device. The second composition may comprise the same or a different cellular culture media. The cells may reside in the disclosed device in a cell chamber. In an aspect, the method comprises wherein the cells are grown or maintained under a parallel gradient. In an aspect, the method comprises wherein the cells are grown or maintained under an opposing gradient.

Disclosed herein are methods for investigating a cellular response to one or more particular physiological states, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring one or more characteristics of the treated cells, and comparing the one or more characteristics of the treated cells to the same characteristics of untreated cells. The second composition may comprise the same or a different cellular culture media. Untreated cells may comprise cells that are not grown or maintained in the presence of a gradient or the comparison may be made to known or published characteristics of cells, such as reference information. For example, the physiological state of oxygen and its effects on cells may be investigated by using gradients that create hypoxic or hyperopic conditions for cells. A cellular response is determined by measuring one or more characteristics of treated cells and comparing the measured characteristics of the treated cells to similar cells that were not treated. The comparison may result in a finding of an inhibited cellular response, an accelerated or enhanced cellular response, or a finding of no response by the cells to the treatment.

Disclosed herein are methods of investigating cellular migration in response to one or more physiological states, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring the migration of the treated cells, and comparing the migration of the treated cells to the migration of untreated cells. The second composition may comprise the same or a different cellular culture media. Untreated cells may comprise cells that are not grown or maintained in the presence of a gradient or the comparison may be made to known or published characteristics of cells, such as reference information. For example, the physiological state of oxygen and its effects on migration of cells may be investigated by using gradients that create hypoxic or hyperopic conditions for cells. A cellular response is determined by measuring the migration of treated cells and comparing the migration of the treated cells to similar cells that were not treated. The comparison may result in a finding of an inhibited migration, an accelerated or enhanced migration, or a finding of no migration by the cells.

Disclosed herein are methods for investigating a cellular response to one or more active agents, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring one or more characteristics of the treated cells, and comparing the one or more characteristics of the treated cells to the same characteristics of untreated cells. The second composition may comprise the same or a different cellular culture media. Untreated cells may comprise cells that are not grown or maintained in the presence of a gradient or the comparison may be made to known or published characteristics of cells, such as reference information. For example, the active agent is a chemotherapeutic agent used to treat cancer cells and its effects on cells may be investigated by using gradients that create hypoxic or hyperopic conditions for cells. A cellular response is determined by measuring one or more characteristics of treated cells and comparing the measured characteristics of the treated cells to similar cells that were not treated. The comparison may result in a finding of an inhibited cellular response, an accelerated or enhanced cellular response, or a finding of no response by the cells to the treatment.

Disclosed herein are methods for investigating cellular migration in response to one or more active agents, comprising establishing, within a disclosed device, one or more gradients in a cell chamber comprising cells to be treated, wherein the one or more gradients are formed by simultaneously introducing into the device a first cellular culture media composition having a certain concentration of a gas, an active agent or both and a second composition having a concentration of a gas, an active agent or both that is/are different from that of the first composition, and measuring the migration of the treated cells, and comparing the migration of the treated cells to the migration of untreated cells. The second composition may comprise the same or a different cellular culture media. Untreated cells may comprise cells that are not grown or maintained in the presence of a gradient or the comparison may be made to known or published characteristics of cells, such as reference information. For example, the active agent is a chemotherapeutic agent used to treat cancer cells and its effects on migration of cells may be investigated by using gradients that create hypoxic or hyperopic conditions for cells. A cellular response is determined by measuring the migration of treated cells and comparing the migration of the treated cells to similar cells that were not treated. The comparison may result in a finding of an inhibited migration, an accelerated or enhanced migration, or a finding of no migration by the cells.

Disclosed herein are methods for investigating reaction kinetics within a gradient of chemicals or active agents. Methods and devices herein may comprise overlapping gradients of active agents. Such methods and devices may comprise compositions comprising active agents that are not compatible with DDMS. Such gradients may or may not comprise gases. Methods include investigations of oxidation/reduction reactions, for example, where oxygen has a role. Such reactions may be carried out in inert conditions, for example, after purging compositions or devices or both with nitrogen or argon gas.

Disclosed herein are kits comprising a disclosed microfluidic device. A kit may further comprise one or more compositions comprising cellular culture media comprising a particular concentration of one or more gases, one or more active agents, or both. A kit may further comprise cells. A kit may further comprise printed or a computer link to instructions for using the components of the kit.

EXAMPLES

Microfluidic Device Fabrication.

The microfluidic chips were fabricated using established soft lithography procedures. The initial design was prepared using AutoCAD software (Autodesk Inc) (FIG. 1A) and subsequently translated on a wafer with SU-8 photoresist using the direct write lithography system Dilase 250 (Kloe, France). SU-8 was first spin-coated onto the substrate, pre-baked, followed by direct write lithography, then subsequently post-baked and developed using the standardized procedures. Liquid PDMS pre-polymer (Sylgard 184, Dow Corning, Mich.) was prepared by thoroughly mixing the base and curing agent (10:1 w/w) and poured onto the mold, degassed and thermally cured at 80° C. in an oven for 90 minutes. PDMS devices were carefully cut with a scalpel and peeled and an 18-gauge flat end needle was used to make the inlets and outlets ports. The devices were then sonicated in isopropyl alcohol for 30 s to remove the debris. Eventually, the channel side of devices were irradiated with oxygen plasma in a plasma asher (Plasma Etch, Carson City, Nev.) and irreversibly bonded to the PDMS/PtOEPK composite film (described in the next section) on a 1×3 inch microscope slide (FIG. 6). Dimensions of the final device were dependent on the design-type, whether single-reservoir or multiple outlets. This was decided through gradient profile data derived from several COMSOL simulations. The dimensions of the microfluidic serpentine channels in the single-reservoir device were 250 (w)×100 (h) μm. For the multiple outlet device, the width of the serpentine channels was reduced to 200 μm and total length was reduced from 1.96 cm to 1.46 cm, effectively reducing residence time per flow rate. For all characterization purposes, 500 μm wide straight channels designs were used.

Sensor Layer Formation.

A modification of the standardized technique established by Nock et. al was used. Polystyrene pellets (MW≈280,000, Sigma-Aldrich, St Lois, Mo.) were dissolved in toluene (Fisher Scientific, Waltham, Mass.) to yield a 7% w/w solution19. PtOEPK dye (Frontier Scientific, Logan, Utah) was then added to form a stock solution at a concentration of 1 mg/ml19. 30 μL of PtOEPK/PS solution was pipetted onto a 1×3 inch microscopic glass slide and spin-coated at 1000 rpm for 30 s and left covered in dark at room temperature to dry for at least 2 hours. After drying, 0.2 gram of PDMS was placed on top of the PtOEPK/PS layer and spin-coated at 2500 rpm to form an approximately 1.5 μm thin layer of PDMS completely covering the dye. The resultant composite layer was then incubated at 40° C. in an oven for approximately 45 minutes (FIG. 6).

Sol-Gel Characterization and 3-Sided Glass Coating.

Sol-gel was prepared by mixing equal volumes of tetra-ethylorthosilicate (Sigma-Aldrich, St Lois, Mo.), methyltri-ethoxysilane (Sigma-Aldrich, St Lois, Mo.), ethanol and pH 4.5 deionized water and left for 24 hours to form a homogenous solution37. To establish a 3-sided glass coating, the sol-gel solution was pipetted through a plasma-treated PDMS device placed in close contact on a non-plasma treated glass slide. The device assembly was then placed on a pre-heated hotplate for the desired time and temperature and gently flushed with compressed air to remove excess unpolymerized silanol. The hotplate was turned off allowing the device to gradually cool down to room temperature. The curing of silanol oligomers (oxide bond formation) primarily occurs on the walls of the plasma-treated microfluidic channels as the hydroxyl groups are only present there. This preferentially creates a three-sided coating as no coating forms on the non-plasma treated bottom glass surface. To determine the optimal coating thickness, curing of silanol oligomers was conducted at varying temperatures and times: of the coating on all three sides was measured through fluorescent images using the EVOS FL Auto microscope (Life Technologies). These results were later validated with the help of a confocal surface profilometer (LEXT OLS4100, Olympus, Japan). Both sets of images were taken by placing the glass coated PDMS devices upside down prior to bonding to the sensor composite layer. To test for leeching, 1 μM rhodamine B solution was infused through the 3 side-coated device assembly and compared with the uncoated controls for a 2-hour duration.

Sensor Layer Calibration.

Sensor-layer characterization and calibration was performed using an Olympus BX-51 fluorescence microscope (Japan). PtOEPK exhibits unique double absorption peaks at 398 nm and 590 nm respectively and an emission peak at 760 nm in the near infrared region (NIR)[30,48]. A customized filter combination with absorption/emission filters at 570/760 nm and a 620 nm dichroic mirror was used for PtOEPK imaging. For gaseous sensor characterization and to test the dynamic sensing ability, industrial grade oxygen and nitrogen gas (Roberts Oxygen, Rockville, Md.) were blown into the straight channels periodically every 20 s. Air (21% O2) was blown though one of the channels constantly for reference. Images were recorded after reaching equilibrium and the respective intensities was analyzed using the Image Processing Toolbox in MATLAB (Mathworks, Natick, Mass.). Intensity was averaged over a region of interest and compared to the reference intensity (nitrogen saturated, ~0% O2). For dissolved oxygen (DO) measurement and characterization, DI water of varying oxygen concentrations were prepared. A customized oxygen and nitrogen delivery system was built and the gases were bubbled into capped glass bottles containing DI water for specific time periods. Bubbling nitrogen and oxygen for 40 minutes and 10 minutes respectively yielded DI water with 0.1 mg/L (0.003 mol/m3) and 19.9 mg/L (0.62 mol/m3) DO content respectively and intermediate DO solutions were obtained by mixing the two stock solutions appropriately. Detection of DO levels was done simultaneously, allowing us to determine exact bubbling periods for both gases. Sensor probe will read/beyond which it fails to . . . once DO levels go beyond 19.9 mg/L, thus, accuracy of the calibration was maintained throughout. Gassed water, kept in 1 ml syringes (BD Hamilton), were infused into the respective devices via 30-gauge blunt needle connected to the Tygon tubing (AAD04091, 0.01" ID×0.03"

TABLE 1

Average glass-coating thickness across different reaction temperatures and times. Bold represents optimal conditions that provide coatings with no unpolymerized spaces and minimal cracks.

| | Temperature (° C.) | | | | |
|---|---|---|---|---|---|
| Time (s) | 60 | 70 | 80 | 90 | 100 |
| 20 | 3.56 ± 1.98 μm | 4.77 ± 1.87 μm | 5.06 ± 1.33 μm | 5.84 ± 1.62 μm | 6.02 ± 0.94 μm |
| 40 | 4.25 ± 1.52 μm | 6.86 ± 0.58 μm | 6.88 ± 0.78 μm | 7.43 ± 0.41 μm | 7.73 ± 1.14 μm |
| 60 | 8.65 ± 1.02 μm | 9.01 ± 1.99 μm | 9.47 ± 1.21 μm | 9.96 ± 0.98 μm | 11.25 ± 0.47 μm |
| 80 | 12.52 ± 0.86 μm | 12.47 ± 2.55 μm | 13.33 ± 0.65 μm | 13.87 ± 1.68 μm | 14.42 ± 1.19 μm |
| 100 | 13.2 ± 2.05 μm | 13.42 ± 1.74 μm | 14.07 ± 1.87 μm | 14.68 ± 2.41 μm | 15.99 ± 2.65 μm |

After cooling, the coated PDMS was peeled off from the slide and plasma bonded to the sensor/PDMS layer (FIG. 6). To confirm the glass-coating formation, sol-gel solution was mixed with fluorescent microspheres (1 μm diameter) (Fluo-Spheres® Carboxylate, ThermoFisher Scientific Inc, Rockville, Md.) prior to introduction into the microfluidic channels at 1:10 (dye: sol-gel) v/v concentration. The thickness OD) using an automated syringe pump (Fusion 100, Chemyx, Stafford, Tex.). DO was measured using a polarographic oxygen meter (MW 600, Milwaukee Instruments, N.C., USA). Signal intensity, I, with respect to O2 concentration is quantified by the Stern-Volmer relationship:

$$I0/I = 1 + K S^{sv}[O2] = 1 + K G^{sv} pO2$$

where $K_s^{sv}$ and $K_G^{sv}$ are the Stern-Volmer constants for solution and gas respectively, $I_0$ represents intensity at 0% oxygen (100% nitrogen), [O2] is oxygen concentration and $pO_2$ is partial pressure of gaseous $O_2$. Plots of relative intensities against DO concentrations and gaseous partial pressure of O2 respectively were extrapolated to validate the Stern-Volmer relationship. Plots of intensity changes during periodic introduction of oxygen and nitrogen (both gaseous and dissolved) were also generated. This data was subsequently used as reference for the intensity variation or changes during the gradient formation in the final fabricated devices.

Gradient Formation and Detection.

Initially, linear flow rates and resulting gradient formation were determined using COMSOL Multiphysics software. These derived conditions were subsequently implemented in the experiments. O2-rich and O2-depleted deionized water was passed at constant flow rates through the microfluidic channels of the final fabricated devices. Diffusion and oxygen detection was monitored using time-lapse epifluorescent microscopy using the Olympus BX-51 fluorescence microscope. The recorded video was imported onto MATLAB and subsequently fragmented into frames. Intensity plots were extracted and analyzed across the desired frames, representing either the reservoir or each chamber, at the different flow rates using Image Processing Toolbox in MATLAB. The respective plots were converted to concentration plots using the previous calibration data, yielding a function curve for each flow rate. Triplicate experiments, along with calibration before each, were conducted and average function plots for respective flow rate were obtained.

Cell Culture and Viability Assay.

Immortalized breast epithelial MCF-12A cells (ATCC, Manassas, Va., USA) were cultured in Dulbecco's Modified Eagle Medium (DMEM) F-12 in T25 flasks under standard 5% CO2 conditions. The channels of the multiple outlet device were first treated with 100 µg/ml fibronectin solution in PBS (F2006, Sigma-Aldrich Co., St. Loius, Mo.) overnight before introducing the cells. The devices were then subsequently washed with the PBS (phosphate buffer saline) and cell suspensions were then introduced (800 cells/µL) into each chamber of the multiple outlet device and left overnight to attach inside a $CO_2$ incubator. Prior to introduction, both cell types were treated with 10 µM CellTracker Green CMGDA dye and 8 µM Hoechst stain (ThermoFisher Scientific, Waltham, Mass., USA) for 30 minutes to stain live cells and nuclei of the cells respectively. After 24 hours, regular (21% oxygen) and deoxygenated media (0%) were introduced simultaneously through the two inlets of the gradient generator at a constant flow-rate of 1.5 µL·min-1 for 8 hours. This was performed inside an on-stage incubator maintained at 5% CO2 and 95% humidity. Time-lapse images were acquired every 20 minutes in each chamber to monitor the cell viability profile using EVOS-FL Auto Cell Imaging System (ThermoFisher Scientific, Waltham, Mass., USA). Image analysis of live cells was conducted using ImageJ (NIH, Bethesda, Md.). The 0% oxygen DMEM F-12 was created by bubbling nitrogen gas into the DMEM F-12 media for approximately one hour. Small amounts of 15 µM HEPES solution was added to both in order to maintain the pH of the media coherent with 5% CO2 before adding to the cell culture. For control purposes, MCF-12A cells were incubated in 96-well plates under both normoxic and hypoxic conditions. The normoxic condition was obtained by incubating the cells in regular conditions of 21% $O_2$ and 5% $CO_2$ inside a regular incubator. Hypoxia was generated by incubating the cells in 95% N2 inside a modular incubator chamber (MIC-101, Billups-Rothenburg Inc, USA). 10 µM CellTracker Red CMTPX dye and 8 µM Hoechst stain were used instead of live cell-staining purposes. See FIGS. 7-9.

Statistical Analysis.

For most experiments, one-tailed t test was performed to determine statistical significance of the data. Functional analysis was conducted in MATLAB to compare COMSOL and experimental data plots for gradient detection. Unless explicitly stated, all experiments were performed in triplicate. Error bars represent standard deviation of the mean.

Deposition and Characterization of Gas Impermeable Sol-Gel Coating.

Figure 2B:
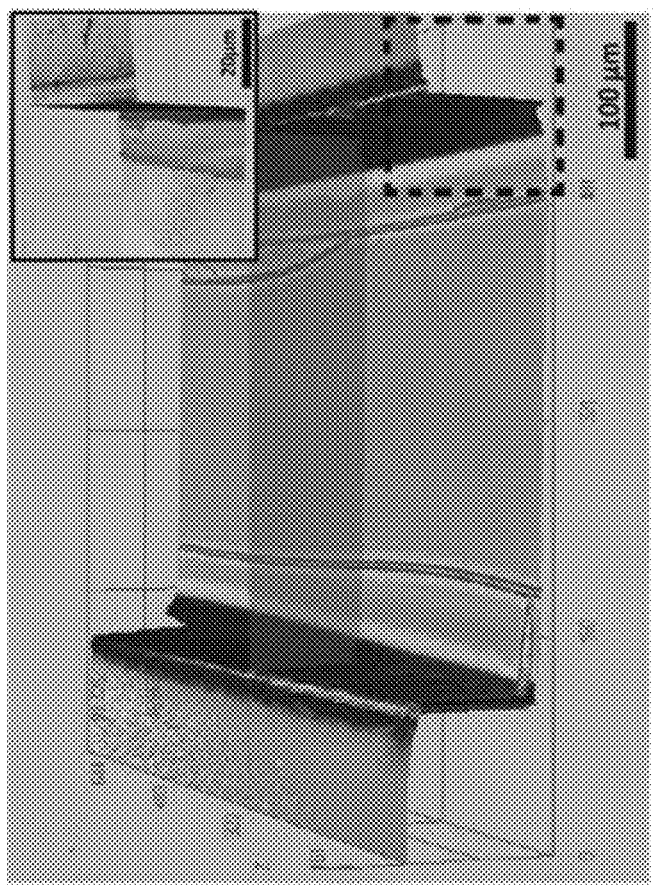
FIG. 2 (consisting of FIGS. 2A-2F) illustrates exemplary details regarding the disclosed glass coating, according to one embodiment of the present disclosure.
Figure 2A:
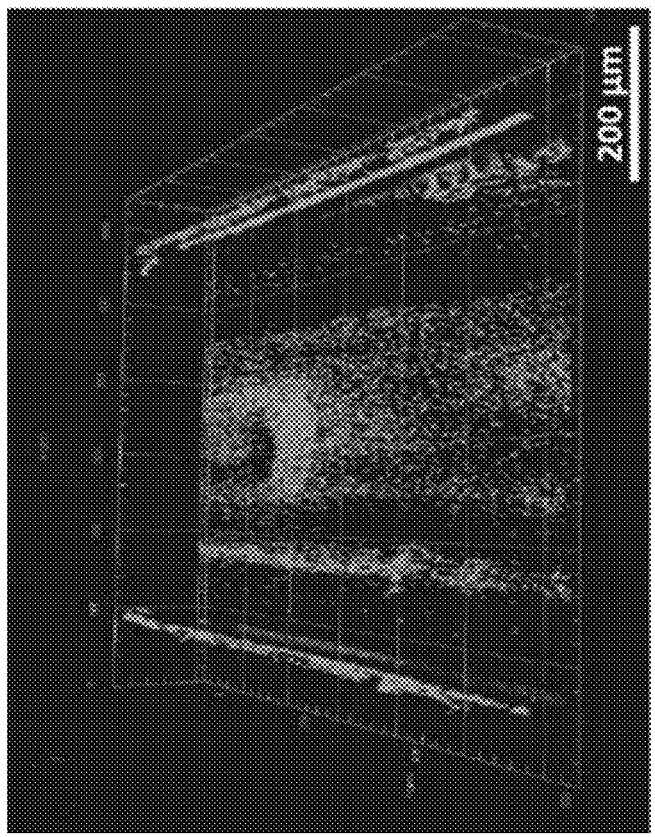
Figure 2D:
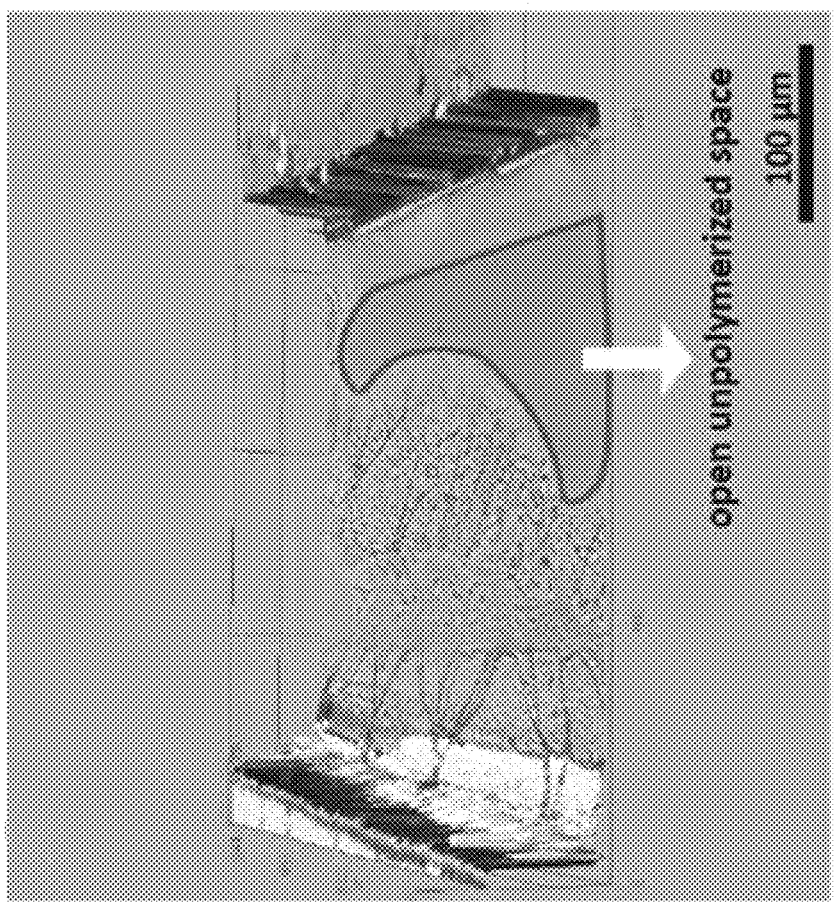

A modification of known sol-gel chemistry was used to deposit the 3-sided silicon dioxide polymer within the channels (See Methods). The polymerization process consisted of 3 main steps; first the hydrolysis of precursor alkoxysilane groups into silanol groups by ethanol, followed by oligomerization of silanol monomers in the presence of an acid[36]. The silanol oligomers then formed hydrogen bonds with the hydroxyl groups present on the walls of the plasma-treated PDMS subtrate[36]. Finally, heat was applied to remove $H_2O$ molecules and form covalent oxide bonds, creating the polymerized glass layer[36]. The 2 key parameters, temperature and reaction time, were characterized to achieve optimal and reproducible coating[36,37]. For this, varying temperatures from 60-100° C. (10.0 increments) and reaction times from 20-100 s (20 s increments) were investigated. To verify the formation of glass coatings, two independent methods were utilized. Initially, fluorescent polystyrene beads were dissolved into the sol-gel solution at a ratio of 1:10 (v/v) prior to the coating formation. Imaging through fluorescent microscopy confirmed the presence of a three-sided glass coating but also facilitated measurements of the coating dimensions (FIG. 2A). This was further validated by imaging the coated channels with a confocal surface profilometer at high resolution (FIG. 2B).

Figure 2C:
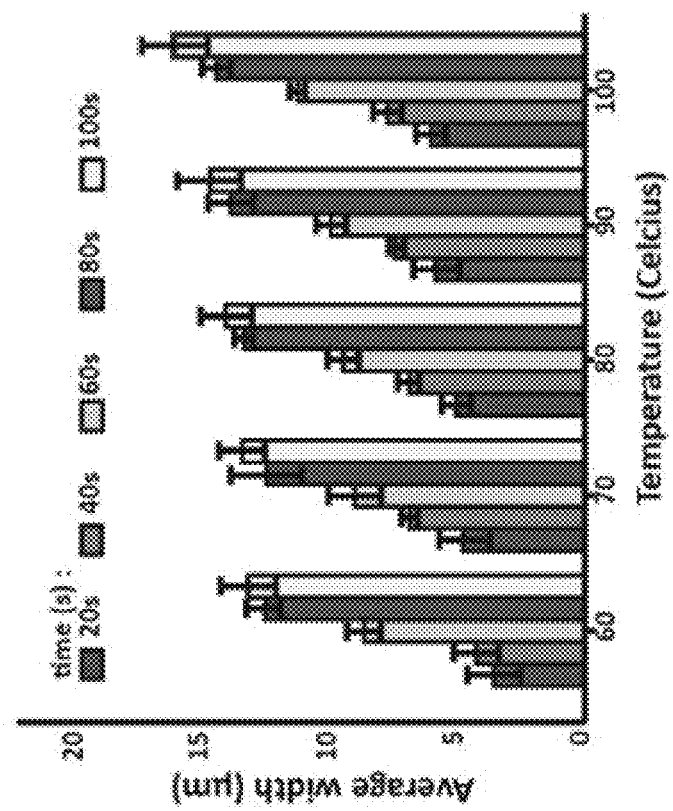

As expected, the average thickness of cured glass-coating increased progressively with both temperature and time ranging from approximately 3-15 µm (FIG. 2C, Table 1). The coating thickness increased exponentially with increasing times while followed a linear pattern with increasing temperatures. Unpolymerized spaces were more prominent when heating at lower temperatures and for shorter time spans (FIG. 2D) whereas the frequency of cracked glass coatings increased significantly as the time or temperature increases (Table 1). It is thought that the crack formation resulted from non-uniform cooling effect when the unpolymerized sol-gel was flushed out using compressed air. The crack formation was significantly more noticeable beyond a coating thickness of approximately 10 µm. For the specific purpose of creating a diffusion barrier and for the channel dimensions of the device, heating at 80.0 for 40 s was identified as an optimal condition that produced glass coating thicknesses of 6.8±0.79 µm with no unpolymerized open spaces and lower frequency of cracks. These conditions were used for all subsequent experiments. Due to thermal gradient along the height of the PDMS device from the hot plate, an arch-like coating was created, i.e. a slightly wider film (by ≈2 µm) at the lower region of the side walls as compared to the top. However, this had little effect on inhibiting gaseous diffusion across the barrier.

Figure 2F:
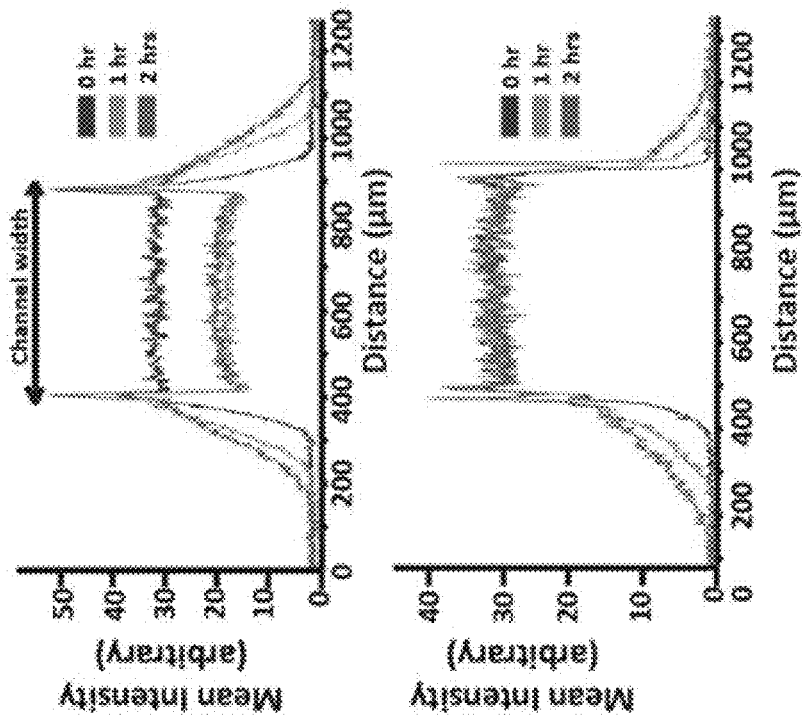
Figure 2E:
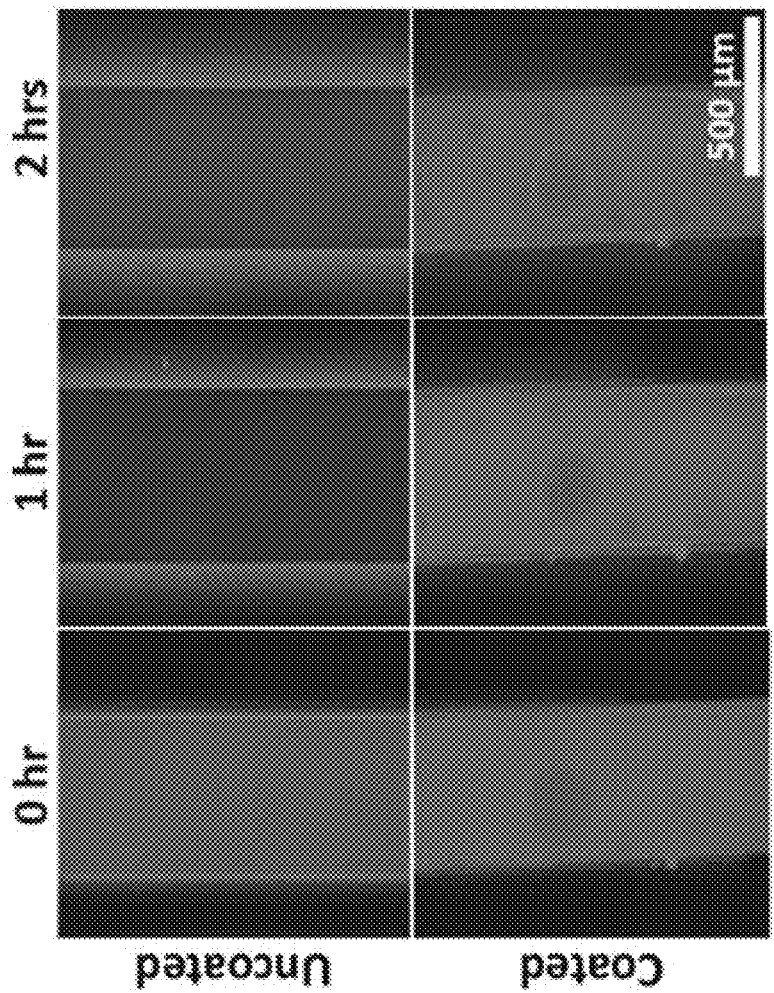

The impermeability of the coating was verified by leeching experiment with rhodamine B solution which is known to diffuse into the PDMS. The average intensity of 1 µM rhodamine B solution within the channels was reduced by approximately 50% of the original fluorescence over a period for 2 hours for the uncoated channels and significant diffusion of the dye outside the channel was observed (FIGS. 2E and 2F). Whereas, no leeching was observed for the glass coated channels and the fluorescence intensity remained unchanged. The 2 peaks represent accumulated rhodamine B solution on the 2 sides of the channel walls.

Integration and Calibration of Oxygen Sensitive PtOEPK Layer.

A 1.3 µm thin film of 7% w/w PtOEPK/PS matrix was spin-coated on a 1×3 inch microscope slide to form the sensor layer[18]. Although spin-coating at lower speeds increased the thickness and PtOEPK molecules available for oxygen quenching, it significantly reduced the spreading surface area of the sensor layer, preventing gradient detection and profiling across the desired regions of both sets of devices. The current spin-coating conditions and concentration of dye (see Methods) creates PtOEPK/PS films with maximum spreading area and uniform thickness (verified with confocal surface profilometer). To prevent possible leeching and cytotoxicity by PtOEPK, when in direct contact with cells 38, an additional 1.5 µm (±0.2) thin layer of PDMS was spin-coated on top of the sensor layer. This created a barrier between cells and PtOEPK while still allowing dissolved oxygen to quickly diffuse through the barrier and interact with underlying PtOEPK. Oxygen diffuses nearly twice as fast through PDMS than water, thus, the vertical diffusion through such negligible distances and subsequent dye quenching would only cause insignificant variations in signal intensity. To perform the calibration of PtOEPK film, a simple straight channel PDMS device was bonded on top of the composite sensor/PDMS layers and pure nitrogen and oxygen gases were introduced successively. Introduction of pure gaseous oxygen resulted in an immediate decrease in the emitted dye luminescence and vice versa for nitrogen (FIG. 3A). Response data for both coated and uncoated channels showed an almost immediate change in luminescence upon alternating the gases, the relative change being superior for coated channels. Gaseous calibration data is coherent with the linear Stern-Volmer relationship for both, with the coated channels demonstrating superior intensity ratio $I_0/I_{100}$ of 3.85 and an improved sensitivity by 20% (FIG. 3C).

Subsequently, primary DO calibration was performed by using DI water of varying oxygen concentrations. No recognizable differences were observed in the DO levels for DI water, phosphate-buffer saline (PBS), or the cell culture media for similar bubbling durations (data not shown). Thus, calibration was performed using DI water to avoid fouling of the sensor probe. To account for photobleaching of the PtOEPK dye, calibration was performed every time prior to the experimentation. Maximum DO detection was limited to 19.9 mg/L due to the resolution of the polarographic meter being used (Milwaukee MW600) and intermediate DO levels were acquired by proportionately mixing 0.1 and 19.9 mg/L DI water. However, this was sufficient to yield a broad and satisfactory range of DO levels, from hypoxic to hyperoxic conditions (0.1 1.7, 7.0, 13.5 and 19.9 mg/L). For reference, atmospheric conditions with 21% partial pressure of oxygen corresponds to 7.8 mg/L of DO levels in most aqueous solutions. Measurements of DO were taken simultaneously during gas bubbling and mixing. The sensor probe utilized here in was incapable of taking measurements beyond 19.9 mg/L and provides an error message, thus enabling determination of exact gas bubbling durations. Plots of relative intensity versus dissolved $O_2$ concentration followed a linear Stern-Volmer trend, with coated devices demonstrating only a slight superiority over the uncoated ones (p<0.05) (FIG. 3D). Since the luminescence intensity depends on the number of PtOEPK molecules available to interact with diffusing oxygen, calibration was performed for each device independently prior to its utilization. These results indicate that the integrated PtOEPK sensor layer can be utilized for real-time sensing of dissolved oxygen and the glass coated devices offer significantly improved detection sensitivity as compared to bare PDMS devices.

Simulation, Characterization and Generation of Oxygen Gradients.

The flow-rates required to produce a linear, working gradient were initially determined using COMSOL simulation for both designs. Taking the diffusivity of oxygen in water into consideration along with incompressible flow and no-slip and non-diffusive boundary conditions, oxygen gradients were simulated at a minimum flow rate of 10 nL/min (FIG. 4). Non-diffusive boundary conditions were assumed to reflect the relative impermeability of the silicon oxide polymer coating. The diffusion co-efficient of oxygen in PDMS at 298.15K or room temperature is approximately 1.7 times greater than water ($3.55 \times 10^{-5}$ cm$^2$/s vs. $2.05 \times 10^{-5}$ cm$^2$/s). Therefore, the coating provides the necessary non-diffusive boundary without which, net oxygen would diffuse across PDMS walls significantly faster as compared to its lateral diffusion across the aqueous streamlines. Hence, at steady state, the concentration of DO at any given space of the microfluidic network is constant proving a continuous stable and linear gradient. In case of the single-reservoir device, though the overall slope of gradient across the reservoir itself was constant {$2.52 \times 10^{-3}$ mg·µm$^{-1}$L$^{-1}$ or $7.8 \times 10^{-5}$ (mol/m$^3$)/µm} irrespective of the flow rate, the long residence time (49 mins) at the minimum flow rate of 10 nL/min caused the gradient to diminish and completely equilibrate by the time it reaches the outlet (FIG. 4). Increasing the flow rate to 1 µL/min significantly improved the stability of the gradient (FIG. 4-(*i*)). This was not observed for the multiple-outlet design as there is no convergence point. Beyond 100 µL/min, diffusion of oxygen within both single- and multiple-outlet devices was dominated by the flow rate such that higher flow rates did not allow sufficient residence time for the diffusion mediated mixing to occur within each split channel network.

Figure 4D:
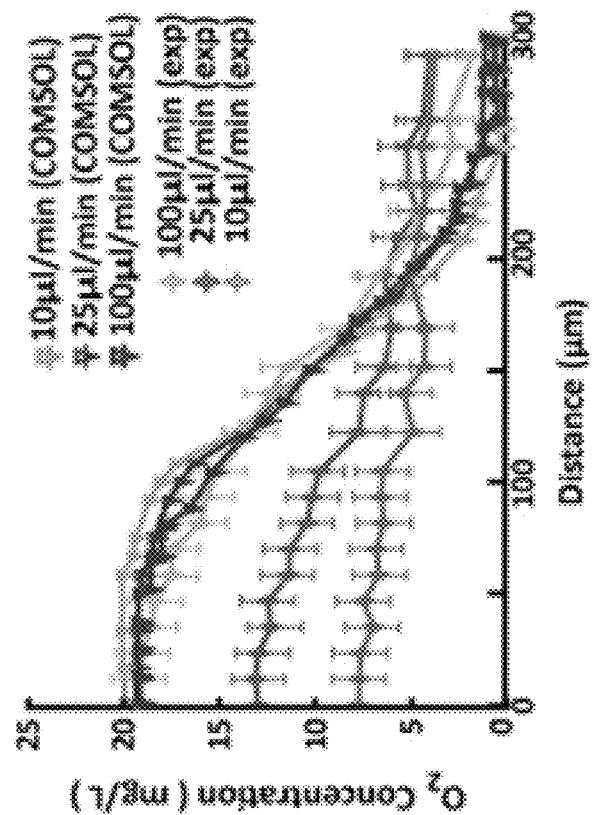
FIG. 4 (consisting of FIGS. 4A-4F) illustrates exemplary oxygen gradients, according to one embodiment of the present disclosure.
Figure 4C:
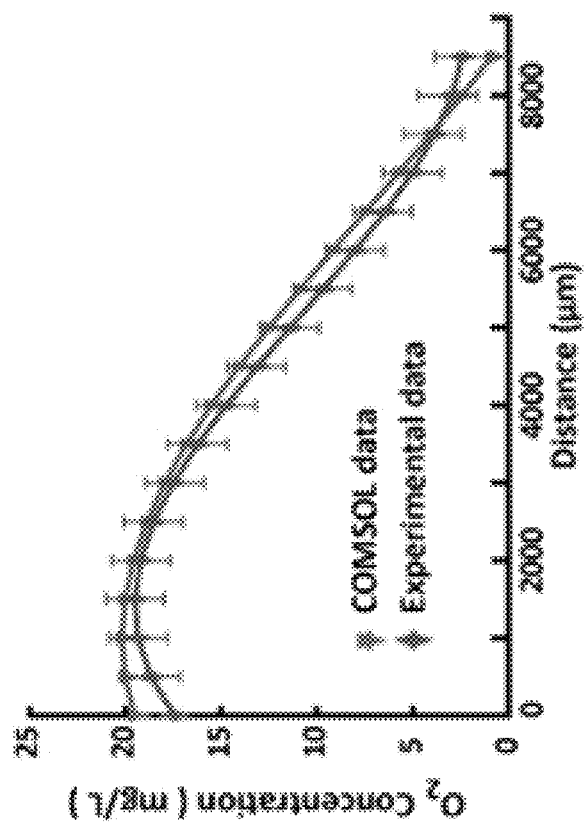
Figure 4F:
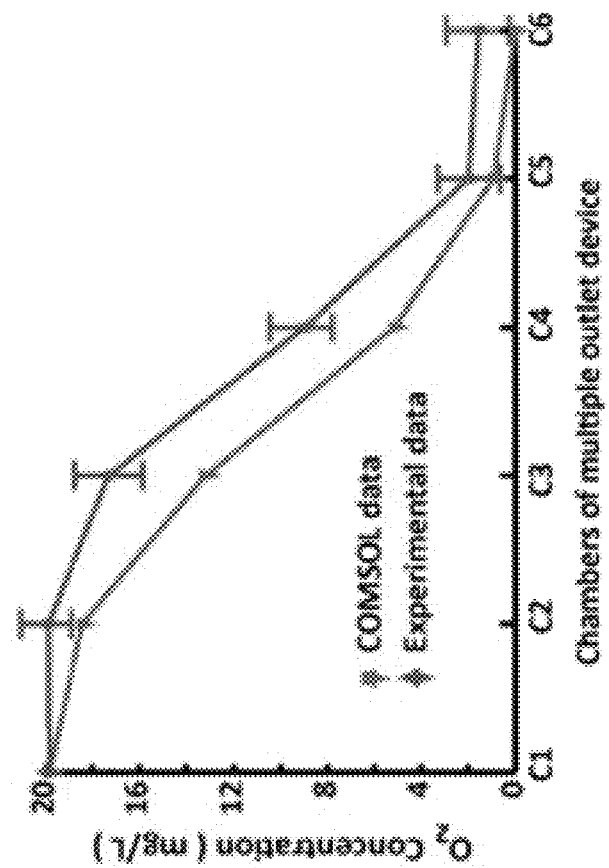
Figure 4E:
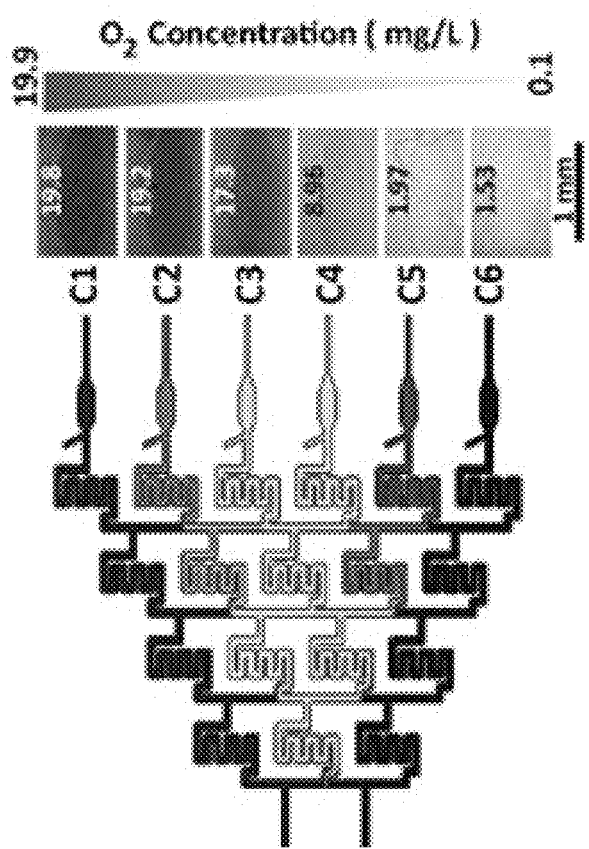

For the given concentration of PtOEPK molecules present under the flow channels in the devices, a minimum flow rate of 1 µL/min was required to produce a detectable oxygen gradient. The overall slope of experimentally generated gradient across the reservoir in the single-reservoir device, at different flow rates was constant and comparable with the COMSOL data, with a slightly diminished value of $2.29 \times 10^{-3}$ mg·µm$^{-1}$L$^{-1}$ or $7.2 \times 10^{-5}$ (mol/m$^3$)/µm (FIG. 4C). Like the COMSOL data, the equilibration trend at low flow rates is observed at the outlet region of the single-reservoir device. The high diffusivity of oxygen in DI water and relatively long residence time (~30 s at 1 µL/min) within the split-channel network causes to quickly equilibrate across streamlines diminishing the slope of the gradient at lower flow rates (FIG. 4-(*iii*)). The most visually prominent concentration profile at the outlet region was produced at 100 µL/min (FIGS. 4-(*iii*) and 4D). The equilibration issue at lower flow rates can be easily resolved by diminishing the dimensions of the required device. Time-based experiments revealed that the intrinsic DO gradient generated within the reservoir was stable for lengthy periods of time, successfully maintain the slope even after 60 minutes (FIG. 7). In case of the multiple-outlet device/design, the slightly smaller dimensions (200 µm wide channels and 1.46 cm in total length) and separated outlets created and confined specific DO concentrations within each chamber of the device (corresponding to the intermediate concentration regimes created by the split channel network). The shortened length reduced the residence time for each flow rate and a significantly improved spatial resolution was observed (FIG. 4E). Slight variations were observed between experimental and COMSOL data at various flow rates (FIG. 4F). Prior to recombining the streams, the ratio of available underlying PtOEPK molecules to oxygen molecules per unit area is significantly higher in region (ii) as compared to region (iii) where the streams are merged into a single channel. Thus, the spatial optical signal coming from region (ii) is also significantly resolved leading to lower observed relative intensities in the outlet channel.

These results validate that stable and linear oxygen gradients can be established with our proposed strategy with simultaneous detection capability. For both sets of designs, gradient stability was maintained over a 1-hour period (FIG. 7), a trend also observed when experimentation was repeated in PBS. Time required for oxygen gradient formation varied according to flow rate, approximately 3-4 minutes at 10 µL/min.

Evaluation of ER Stress Under Gradients of Oxygen.

Hypoxia is known to induce unfolded protein response and increased endoplasmic reticulum (ER) stress in many cell types including the breast epithelial cell line MDA-MB-468. To explore the effects of hypoxic gradients on ER stress of these cells and to evaluate the overall applicability of the microfluidic hypoxia platform, MDA-MB-468 cells were cultured within region I and exposed to a gradient of oxygen from 0-21%. Thioflavin T (indicator of ER stress) induced fluorescence linearly increased with increasing levels of hypoxia across the width of region I (FIGS. 5A and 5B) with a 4-fold increase from baseline (t=0 hour) fluorescence after 6 hours in the most hypoxic location (FIG. 5C). Time-lapse imaging also indicated a gradual but consistent increase in fluorescence intensity throughout region I. MDA-MB-468 cells incubated in a separate device underwent the identical procedure with the absence of an oxygen gradient yielding a relatively constant fluorescence of thioflavin T throughout region I (FIG. 5C). The observations were coherent with control experiments conducted in well-plates and with the literature. These results demonstrate applicability of the hypoxia gradient generation strategy for a variety of real-time biological studies.

Viability Analysis of Mammary Epithelial Cells MCF-12A Under Gradients of Oxygen.

The viability control experiments were conducted in 96 well-plates with MCF-12A cells being incubated in normal (21% oxygen & 5% $CO_2$) and hypoxic (95% nitrogen & 5% $CO_2$) conditions respectively, while another group was seeded inside the multiple-outlet device and left overnight to attach (FIGS. 5D and 5E). Due to hypoxic stress, the viability of MCF-12A cells followed a negative correlation with declining oxygen levels (FIGS. 5D and 5E). Despite the heightened glucose quantity in DMEM-F12 media, relative oxygen concentrations below critical level with alter physiological functions of regular cells and diminish uptake. As such, after the 8-hour incubation period, live-cell viability of hypoxia treated MCF-12A cells in the 96-well plate control setup was reduced to almost 23% compared to the 92% viability observed in regular MCF-12A cells (FIG. 8). In contrast, viability of the cells in the hypoxic chambers of the multiple outlet device reduced below 20%, yielding approximately 85% mortality. Fluorescent intensity of green CMFDA reduced drastically from C1 (normal) to C6 (most hypoxic) over an 8-hour incubation period, with the cells seeded in C6 suffering a mortality of approximately 88%, which was significantly superior to the data derived from the 96-well plate experiments (FIG. 8). Though DMEM contains heightened levels of glucose to avoid starvation, environmental DO levels below the critical oxygen concentration of 1% adversely affects nutrient uptake by cells and eventually induces apoptosis[40]. These results demonstrate potential applicability of our proposed microfluidic gradient generation strategy for a variety of hypoxia studies.

Disclosed herein are stable microfluidic gaseous gradients suitable for a variety of applications. Integration of real-time sensing capability and three-sided glass coating provided a versatile platform to study the effects of oxygen or any other gas on cell functions. Existing microfluidic oxygen gradient generation strategies utilize multilayer PDMS devices with gaseous inlets that are relatively more complex to fabricate and operate, and makes these devices susceptible to bubble formation. Devices and methods disclosed herein utilized a single layer device and a straightforward operating principle. Using two different pre-gassed tissue culture media solutions in gas-tight syringes, oxygen gradients of various spatial resolutions can be rapidly and conveniently established. The requirement of a separate gas layer or multiple gas inlets was thereby completely eradicated. The integrated PtOEPK/PS sensor layer was highly sensitive to changes in oxygen concentrations. Polystyrene prevents leeching of the luminescent PtOEPK into the media, therefore any activity (whether cytotoxic or protein expression) can only be attributed to the varying oxygen conditions generated. Despite the fact that oxygen diffuses nearly twice as fast through PDMS than water, the impermeability of the glass coating and the thin membrane ensures constant net dissolved oxygen flowing through the aqueous buffer at any given point in time or location. The thin layer of PDMS on top of PtOEPK/PS layer allowed instant diffusion of oxygen and consequent saturation of the dye, while enabling bonding of the top PDMS device to the substrate and a clear separation from cultured cells. Since the emission spectrum of PtOEPK is near the near IR range (peak 760 nm) of the spectrum, the entire experiment (oxygen-gradient detection) can be conducted in a non-darkroom environment. The photostability of PtOEPK facilitated prolonged cell-based experimentation without noticeable photobleaching or diminished detection sensitivity. Although, the characterization curves presented here verified that integration of the sensor layer was not necessary and the gradient generation approach can also be utilized without the need for PtOEPK deposition step, if DO detection is not critical to the investigation. As previously mentioned, due to high diffusivity of oxygen in water and long residence time, the spatial resolution of oxygen concentration gradient was diminished at very low flow rates (less than 10 µL/min). This can be resolved by reducing the channel lengths within the split-channel network of the device, as demonstrated for the multiple outlet device. The technique therefore enabled detection of ambient oxygen with an enormous range of oxygen concentrations, only limited by the capability of the initial calibration electrode, and capacity of the fluid to hold oxygen. For this investigation, the range was between 19.9 mg/L to 0 mg/L. Adapting Henry's Law, the measurable percentage oxygen saturation in DI water ranged from 0% to 240%. Therefore, the current device can be used to explore the effects of extreme oxygen conditions on a plethora of microscopic aquatic species or flora, fully demonstrating its versatility and potential. The activity of marine heterotrophic bacterioplankton is highly dependent on partial $CO_2$ pressure, and E.coli metabolism is highly dependent on minute changes in oxygen concentration. Therefore, with appropriate modifications in design, both aerobic and anaerobic analysis of bacteria under the effect of $CO_2$ or $O_2$ concentration gradients can be conveniently explored. Additionally, the split-channel devices have been shown to generate gradients of multiple chemicals. Similar strategies can be adapted to utilize pre-gassed solutions of two or more gases to generate more complex gradients extending the versatility of the proposed approach.

Cell migration in response to oxygen gradients has been attributed to cancer progression. However, random motility of cells can also be disadvantageous in studies where migration is not the focus of investigation yet cells tend to leave the field of view under oxygen gradients. Two different designs, one with a single outlet channel that can be used for migration studies and another with multi-outlet channels where cells remain confined within chambers containing a singular oxygen concentration were disclosed herein. Since the chambers are physically separated, the cells are not able to migrate to oxygen rich areas. Therefore, the technique allowed performance of the functions of several specialized $O_2$ incubators at once without requiring expensive infrastructure. Moreover, since the oxygen-tension profile in multichambered devices ranged from 21%-0%, it was effective in recreating and consistently reproducing the physiological microenvironments of pathological conditions such as ischemia or the tumor microenvironment. Thus, acquisition of drug resistance by tumor cells under hypoxic conditions can be conveniently investigated. Depending on the requirement, hyperoxic oxygen conditions can also be generated to observe their subsequent effects. Due to the significantly amplified HIF-1α expression, glycolysis and mitochondrial activity of tumor cells compared to normal cells, MCF-12A cells were selected instead as the relative consumption of oxygen from cellular respiration of these epithelial cells would not significantly affect local DO levels as media is being adequately replenished. To observe metabolic changes and quantify changes in environmental oxygen via tumor cell respiration in potential experiments using the current platform, device modifications will be necessary.

One of the biggest limitations of PDMS-based microfluidic devices is the inability to conduct experiments with organic solvents. PDMS swells in contact with several organic solvents such as toluene significantly altering the channel dimensions within the device. The current methods disclosed not only enable the use of such solvents, but also allows convenient optimization of the thickness of the glass coating per the design of the microfluidic device. Adhesion and diffusion of biomolecules within the hydrophobic PDMS surfaces can also be significantly inhibited. Despite the numerous benefits the technique, cellular experimentation is restricted to attached or fixed cells. Experiments requiring cell suspensions within media cannot be conducted as all the cells would be immediately flushed out.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. A microfluidic device, comprising:
    a glass or polymethylmethacrylate substrate; and
    a layer of polydimethylsiloxane (PDMS) on and bonded to the substrate, the layer of PDMS comprising at least one reservoir having an inner wall of PDMS, the reservoir comprising:
        at least two media inlets;
        at least one cell chamber;
        at least one cell inlet connected to the cell chamber;
        at least one serpentine mixing channel network from the at least two media inlets to the cell chamber; and
        at least one media outlet connected to the cell chamber;
    wherein
        the at least one serpentine mixing channel network is configured to provide a media gradient across the cell chamber, and
        the inner PDMS wall of the at least one serpentine mixing channel network is coated with a glass substance that inhibits diffusion of a gas within the channel network.

2. The device of claim 1, further comprising an oxygen sensor on the substrate adjacent to the cell chamber.

3. The device of claim 2, wherein the oxygen sensor comprises a platinum(II) octaethylporphyrin ketone (PtOEPK)-based sensor layer.

4. The device of claim 2, further comprising a PDMS membrane on the oxygen sensor.

5. A method of growing or maintaining cells under parallel or opposing gradients of gases, active agents, or both in a microfluidic device according to claim 1, comprising:
    introducing cells into the microfluidic device through the at least one cell inlet;
    providing a first cellular culture media composition comprising a first certain concentration of a first gas, a first active agent, or both to a first media inlet of the at least two media inlets;
    providing a second cellular culture media composition different from the first cellular culture media composition comprising a second certain concentration of a second gas, a second active agent, or both to a second media inlet of the at least two media inlets;
    allowing the cells to grow or be maintained in the microfluidic device in a cellular culture media gradient composition; and evaluating the cells across the cellular culture media gradient.

6. The method of claim 5, wherein the cells comprise cancer cells.

7. The method of claim 6, wherein the first and second cellular culture media compositions comprise anticancer drugs.

8. A kit, comprising: the microfluidic device of claim 1; and instructions for: introducing cells into the microfluidic device; providing a first cellular culture media composition comprising a first certain concentration of a first gas, a first active agent, or both; providing a second cellular culture media composition comprising a second certain concentration of a second gas, a second active agent, or both, wherein the second cellular culture media composition is different from the first cellular culture media composition; and allowing the cells to grow or be maintained in the microfluidic device.

* * * * *